United States Patent
Danz et al.

(10) Patent No.: US 11,542,221 B2
(45) Date of Patent: Jan. 3, 2023

(54) α, α-DISUBSTITUTED CARBOXYLIC ACID ESTERS FOR USE AS AROMA CHEMICALS

(71) Applicant: BASF SE, Ludwigshafen am Rhein (DE)

(72) Inventors: Manuel Danz, Ludwigshafen am Rhein (DE); Ralf Pelzer, Lampertheim (DE); Miriam Bru Roig, Ludwigshafen am Rhein (DE); Florian Garlichs, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/261,420

(22) PCT Filed: Jul. 19, 2019

(86) PCT No.: PCT/EP2019/069536
§ 371 (c)(1),
(2) Date: Jan. 19, 2021

(87) PCT Pub. No.: WO2020/016421
PCT Pub. Date: Jan. 23, 2020

(65) Prior Publication Data
US 2021/0309599 A1    Oct. 7, 2021

(30) Foreign Application Priority Data

Jul. 19, 2018    (EP) ..................... 18184469

(51) Int. Cl.
*C07C 69/24*     (2006.01)
*A61Q 13/00*    (2006.01)

(52) U.S. Cl.
CPC .............. *C07C 69/24* (2013.01); *A61Q 13/00* (2013.01)

(58) Field of Classification Search
CPC ................................ C07C 69/24; A61Q 13/00
See application file for complete search history.

(56) References Cited

U.S. PATENT DOCUMENTS

| | | | | |
|---|---|---|---|---|
| 2,424,653 | A * | 7/1947 | Ford | C07C 67/38 560/233 |
| 4,126,585 | A * | 11/1978 | Conrad | C11B 9/0019 428/350 |
| 5,756,856 | A | 5/1998 | Bueschken et al. | |
| 9,211,243 | B2 * | 12/2015 | Auguste | A61Q 19/00 |

FOREIGN PATENT DOCUMENTS

| DE | 2008128 A1 | 9/1971 | |
|---|---|---|---|
| EP | 134613 A1 * | 3/1985 | ............. C07C 69/24 |

* cited by examiner

*Primary Examiner* — Yate' K Cutliff
(74) *Attorney, Agent, or Firm* — Faegre Drinker Biddle & Reath LLP

(57) ABSTRACT

The present invention relates to the use of an α,α-disubstituted carboxylic acid ester of the general formula (I) wherein the variables are as defined in the claims and the description, or of mixtures of two or more of these α,α-disubstituted carboxylic acid esters or of a stereoisomer thereof or of a mixture of two or more stereoisomers thereof as aroma chemicals; to the use thereof for modifying the scent character of a fragranced composition; to an aroma chemical composition containing an α,α-disubstituted carboxylic acid ester of the general formula (I) or a mixture of two or more of said α,α-disubstituted carboxylic acid esters or of a stereoisomer thereof or of a mixture of two or more stereoisomers thereof; and to a method of preparing a fragranced composition or for modifying the scent character of a fragranced composition. The invention further relates to specific mixtures of α,α-disubstituted carboxylic acid esters of the general formula (I).

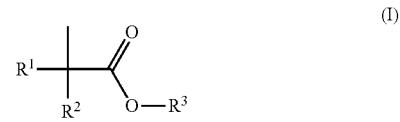

21 Claims, No Drawings

α,α-DISUBSTITUTED CARBOXYLIC ACID ESTERS FOR USE AS AROMA CHEMICALS

CROSS-REFERENCE TO RELATED APPLICATIONS

This application is a national stage application (under 35 U.S.C. § 371) of PCT/EP2019/069536, filed Jul. 19, 2019, which claims benefit of European Application No. 18184469.7, filed Jul. 19, 2018, both of which are incorporated herein by reference in their entirety.

The present invention relates to the use of an α,α-disubstituted carboxylic acid ester or of mixtures of two or more α,α-disubstituted carboxylic acid esters or of a stereoisomer thereof or of a mixture of two or more stereoisomers thereof as aroma chemicals; to the use thereof for modifying the scent character of a fragranced composition; to an aroma chemical composition containing an α,α-disubstituted carboxylic acid ester or a mixture of two or more of said α,α-disubstituted carboxylic acid esters or of a stereoisomer thereof or of a mixture of two or more stereoisomers thereof; and to a method of preparing a fragranced composition or for modifying the scent character of a fragranced composition.

The invention further relates to specific α,α-disubstituted carboxylic acid esters.

TECHNICAL BACKGROUND

Aroma chemicals, especially fragrances, are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest to create synthetic substances which have organoleptic properties that resemble more expensive natural fragrances or which have novel and interesting organoleptic profiles.

Despite a large number of already existing synthetic aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other fragrances, a higher stability under certain application conditions, a higher extendability, a better higher substantivity, etc.

However, since even small changes in chemical structure bring about massive changes in the sensory properties such as odor and also taste, the targeted search for substances with certain sensory properties such as a certain odor is extremely difficult. The search for new fragrances and flavorings is therefore in most cases difficult and laborious without knowing whether a substance with the desired odor and/or taste will even actually be found.

Some α,α-disubstituted carboxylic acid esters are commercially available.

For example isomer mixtures of vinyl esters of highly branched $C_9$- and $C_{10}$-carboxylic acids are commercially available from the company Hexion under the brand name VeoVa™ 9 monomer and VeoVa™ 10 monomer. They are used as monomer building blocks for the manufacture of polymers and help to impart a low glass transition temperature and good chemical and UV resistance.

It was the object of the present invention to provide new aroma chemicals. These should have pleasant organoleptic properties. It was a further object of the present invention to provide substances which can be used as an aroma chemical in ready-to-use compositions. In particular, odor-intensive substances having a pleasant odor are sought. Furthermore, they should be combinable with other aroma chemicals, allowing the creation of novel advantageous sensory profiles. In addition, these aroma chemicals should be obtainable from readily available starting materials, allowing their fast and economic manufacturing, and should be free of toxicological concerns.

A further, specific object of the present invention was to provide specific compounds or compound mixtures, which have a berry odor note (such as blueberry and/or redberry odor note) and/or a spicy odor note.

This object is achieved by the compound of formula (I) as shown below or mixtures thereof or stereoisomers thereof.

SUMMARY OF THE INVENTION

The invention relates to the use of a compound of the general formula (I)

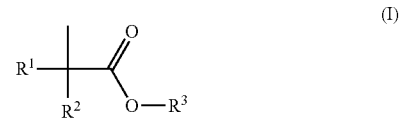

wherein $R^1$ and $R^2$, independently of one another, are $C_1$-$C_8$-alkyl, and $R^3$ is $C_1$-$C_4$-alkyl or $C_2$-$C_4$-alkenyl, where the total number of carbon atoms of the radicals $R^1$ and $R^2$ is in the range of from 3 to 9, or of a mixture of two or more compounds of the general formula (I), or of a stereoisomer thereof or of a mixture of two or more stereoisomers thereof, as an aroma chemical.

Another aspect of the invention is the use of a compound of formula (I) or a mixture of two or more compounds of formula (I) or a stereoisomer thereof or a mixture of two or more stereoisomers thereof for modifying the scent character of a fragranced composition, e.g. of a fragranced ready-to-use composition.

Yet another aspect of the invention is an aroma chemical composition comprising
- a compound of formula (I) or a mixture of two or more compounds of the general formula (I) or a stereoisomer thereof or a mixture of two or more stereoisomers thereof, as defined herein, and
- at least one further aroma chemical and/or a non-aroma chemical carrier, where the non-aroma chemical carrier is in particular selected from the group consisting of surfactants, oil components and solvents.

The invention also relates to a method for preparing a fragranced composition, e.g. a fragranced ready-to-use composition, or for modifying the scent character of a fragranced composition, e.g. of a fragranced ready-to-use composition, comprising incorporating a compound of formula (I) or a mixture of two or more compounds of the general formula (I) or a stereoisomer thereof or a mixture of two or more stereoisomers thereof into said composition.

The invention also relates to a method for preparing a compound of formula (I) or a mixture thereof or a stereoisomer thereof or a mixture of two or more stereoisomers thereof; and to mixtures of two or more compounds of formula (I) obtainable by this method.

Further, the invention relates to a mixture of two or more different compounds of the general formula (I)

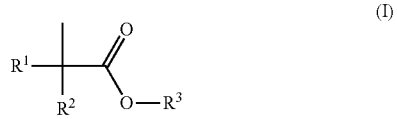

wherein
R$^1$ and R$^2$, independently of one another, are C$_1$-C$_8$-alkyl, and
R$^3$ is C$_1$-C$_4$-alkyl,
where the total number of carbon atoms of the radicals R$^1$ and R$^2$ is in the range of from 3 to 9,
or of a stereoisomer thereof or of a mixture of two or more stereoisomers thereof.

The compounds of formula (I) as well as mixtures of two or more compounds of formula (I), their stereoisomers and the mixtures of their stereoisomers possess advantageous organoleptic properties, in particular a pleasant odor. Therefore, they can be favorably used as an aroma chemical for example in perfume compositions, body care compositions (including cosmetic compositions), products for oral and dental hygiene, hygiene articles, cleaning compositions (including dishwashing compositions), textile detergent compositions, compositions for scent dispensers, foods, food supplements, pharmaceutical compositions and crop protection compositions.

By virtue of their physical properties, the compounds of formula (I) as well as mixtures of two or more compounds of formula (I), their stereoisomers and the mixtures of their stereoisomers have particularly good, virtually universal solvent properties for other fragrances and other customary ingredients in fragranced ready-to-use compositions such as, in particular, perfume compositions. Therefore, the compounds of formula (I) as well as mixtures of two or more compounds of formula (I), their stereoisomers and the mixtures of their stereoisomers are favorably combinable with other aroma chemicals, allowing, in particular, the creation of perfume compositions having novel advantageous sensory profiles.

Furthermore, the compounds of formula (I) as well as mixtures of two or more compounds of formula (I), their stereoisomers and the mixtures of their stereoisomers can be produced in good yields and purities by a simple synthesis which generally requires only one step, starting from readily available starting compounds. Thus, the compounds of formula (I) as well as mixtures of two or more compounds of formula (I), their stereoisomers and the mixtures of their stereoisomers can be produced in large scales and in a simple and cost-efficient manner.

DETAILED DESCRIPTION OF THE INVENTION

In mixtures of two or more compounds of the formula (I) the two or more different compounds (I) differ in the definition of at least one of the radicals R$^1$, R$^2$ and R$^3$. The difference is not only based on stereochemistry. If for example two compounds (I) differ only in the definition of R$^1$, the two radicals R$^1$ have either different chain lengths or are structural or constitutional isomers, or differ in both properties, i.e. have different chain lengths and are simultaneously structural or constitutional isomers. The same applies if two compounds differ only in the definition of R$^2$. If two compounds differ only in the definition of R$^3$, a further difference may be that one radical is saturated and the other unsaturated.

In the context of the present invention, the term "alkyl" as used herein refers to a linear or branched saturated hydrocarbon radicals having 1 to 3 ("C$_1$-C$_3$-alkyl"), 1 to 4 ("C$_1$-C$_4$-alkyl"), 2 to 4 ("C$_2$-C$_4$-alkyl"), 3 to 4 ("C$_3$-C$_4$-alkyl"), 1 to 6 ("C$_1$-C$_6$-alkyl") or 1 to 8 ("C$_1$-C$_8$-alkyl") carbon atoms. C$_1$-C$_3$-Alkyl is methyl, ethyl, propyl and isopropyl. C$_1$-C$_4$-Alkyl is additionally n-butyl, 1-methylpropyl (sec-butyl), 2-methylpropyl (isobutyl) or 1,1-dimethylethyl (tert-butyl). C$_1$-C$_6$-Alkyl is additionally also, for example, n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. C$_1$-C$_8$-Alkyl is additionally also, for example, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,1,2,2,-tetramethylpropyl, 1-ethyl-2-methylbutyl, 1-ethyl-3-methylbutyl, 2-ethyl-3-methylbutyl, 1-ethyl-2,2-dimethylpropyl, n-octyl, isooctyl, or 2-ethylhexyl.

In the context of the present invention, the term "branched alkyl" as used herein refers to a branched saturated hydrocarbon radicals having 3 to 5 ("branched C$_3$-C$_5$-alkyl"), 3 to 6 ("branched C$_3$-C$_6$-alkyl") or 3 to 8 ("C$_3$-C$_8$-alkyl") carbon atoms. Branched C$_3$-C$_5$-alkyl is for example isopropyl, 1-methylpropyl (sec-butyl), 2-methylpropyl (isobutyl), 1,1-dimethylethyl (tert-butyl), 1-methylbutyl, 2-methylbutyl, 3-methylbutyl, 2,2-dimethylpropyl, 1-ethylpropyl, 1,1-dimethylpropyl or 1,2-dimethylpropyl. Branched C$_3$-C$_6$-alkyl is additionally also, for example, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. Branched C$_3$-C$_8$-alkyl is additionally also, for example, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,1,2,2,-tetramethylpropyl, 1-ethyl-2-methylbutyl, 1-ethyl-3-methylbutyl, 2-ethyl-3-methylbutyl, 1-ethyl-2,2-dimethylpropyl, isooctyl, or 2-ethylhexyl. Branched alkyl with 6 or 7 carbon atoms ("branched C$_6$-C$_7$-alkyl") is e.g. 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,1,2,2,-tetramethylpropyl, 1-ethyl-2-methylbutyl, 1-ethyl-3-methylbutyl, 2-ethyl-3-methylbutyl, 1-ethyl-2,2-dimethylpropyl and the like.

In the context of the present invention, the term "$C_2$-$C_4$-alkenyl" as used herein refers to monounsaturated straight-chain or branched hydrocarbon radicals having 2 to 4 carbon atoms and a double bond in any position. Examples for $C_2$-$C_4$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

The term "stereoisomers" encompasses optical isomers, such as enantiomers or diastereomers, the latter existing due to more than one stereogenic center in the molecule, as well as geometrical isomers (cis/trans isomers) as a specific form of diastereomers. The compounds of the formula (I), where $R^1$ and $R^2$ are different and are not methyl, have at least one stereogenic center, namely the carbon atom in alpha-position to the carboxylate-group carrying the radicals $R^1$ and $R^2$. Furthermore, the radicals $R^1$ and $R^2$ may also have at least one stereogenic center, for example if $R^1$ and/or $R^2$ are selected from 1-methylpropyl, 1-methylbutyl, 2-methylbutyl, 1-ethylpropyl, 1,2-dimethylpropyl, 1,2-dimethylbutyl, 1,3-dimethylbutyl, 2,3-dimethylbutyl, 1-ethylbutyl, 2-ethylbutyl, 1-ethyl-1-methylpropyl, or 1-ethyl-2-methylpropyl. The invention provides both the pure enantiomers or diastereomers and mixtures thereof and the use according to the invention of the pure enantiomers or pure diastereomers of the compound (I) or mixtures thereof.

In the present context, the term "compound (I)" or "compound of formula (I)", when not defined as a specific stereoisomer or a specific mixture of stereoisomers, refers to the form of the compound as it is obtained in a non-stereoselective method used for its production. The term is however also used if it is not necessary or not possible to specify in more detail the stereochemistry of the compound (I).

Preferably, $R^1$ and $R^2$, independently of one another, are selected from the group consisting of methyl, ethyl, n-propyl, n-butyl and branched $C_3$-$C_8$-alkyl. In particular, $R^1$ and $R^2$, independently of one another, are selected from the group consisting of methyl, ethyl and branched $C_3$-$C_6$-alkyl.

In a specific embodiment of compounds (I),
$R^1$ is selected from $C_1$-$C_4$-alkyl, and
$R^2$ is selected from branched $C_3$-$C_8$-alkyl.
In a more specific embodiment of compounds (I),
$R^1$ is selected from $C_1$-$C_4$-alkyl, and
$R^2$ is selected from branched $C_3$-$C_6$-alkyl.
In an even more specific embodiment of compounds (I),
$R^1$ is selected from $C_1$-$C_3$-alkyl and
$R^2$ is selected from branched $C_3$-$C_5$-alkyl.
In this more specific embodiment of compounds (I) $R^1$ is in particular methyl.
In another even more specific embodiment of compounds (I),
$R^1$ is preferably selected from $C_1$-$C_3$-alkyl, and
$R^2$ is preferably selected from branched $C_4$-$C_6$-alkyl.

It is further preferred that in the above mentioned embodiments, the branching in the radicals $R^2$ is located at least in the α- and/or the β-position to the attachment point of the radical $R^2$ to the rest of the molecule.

Preferably, $R^3$ is $C_1$-$C_4$-alkyl. In particular, $R^3$ is methyl or ethyl. Specially, $R^3$ is ethyl.

Preferably, the total number of carbon atoms of the radicals $R^1$ and $R^2$ in the compound of the general formula (I) is in the range of from 4 to 8. More preferably, the total number of carbon atoms of the radicals $R^1$ and $R^2$ in the compound of the general formula (I) is in the range of from 5 to 7. In particular, the total number of carbon atoms of the radicals $R^1$ and $R^2$ in the compound of the general formula (I) is in the range of from 6 to 7.

In a preferred embodiment, in compounds (I)
$R^1$ and $R^2$, independently of one another, are selected from methyl, ethyl and branched $C_3$-$C_8$-alkyl, and
$R^3$ is $C_1$-$C_4$-alkyl,
where the total number of carbon atoms of the radicals $R^1$ and $R^2$ is in the range of from 4 to 8.

In a preferred embodiment, in compounds (I)
$R^1$ is selected from $C_1$-$C_4$-alkyl,
$R^2$ is selected from branched $C_3$-$C_6$-alkyl,
$R^3$ is $C_1$-$C_4$-alkyl,
where the total number of carbon atoms of the radicals $R^1$ and $R^2$ is in the range of from 4 to 8.

In a more preferred embodiment, in compounds (I)
$R^1$ is selected from $C_1$-$C_3$-alkyl,
$R^2$ is selected from branched $C_3$-$C_5$-alkyl, and
$R^3$ is $C_1$-$C_4$-alkyl,
where the total number of carbon atoms of the radicals $R^1$ and $R^2$ is in the range of from 4 to 8.

In another more preferred embodiment, in compounds (I)
$R^1$ is selected from $C_1$-$C_3$-alkyl,
$R^2$ is selected from branched $C_4$-$C_6$-alkyl, and
$R^3$ is $C_1$-$C_4$-alkyl,
where the total number of carbon atoms of the radicals $R^1$ and $R^2$ is in the range of from 4 to 8.

In an even more preferred embodiment, in compounds (I)
$R^1$ and $R^2$, independently of one another, are selected from methyl, ethyl and branched $C_3$-$C_6$-alkyl, and
$R^3$ is $C_1$-$C_4$-alkyl,
where the total number of carbon atoms of the radicals $R^1$ and $R^2$ is in the range of from 6 to 7.

In a specific embodiment, in compounds (I)
$R^1$ is selected from $C_1$-$C_4$-alkyl,
$R^2$ is selected from branched $C_3$-$C_6$-alkyl,
$R^3$ is $C_1$-$C_4$-alkyl,
where the total number of carbon atoms of the radicals $R^1$ and $R^2$ is in the range of from 6 to 7.

In a more specific embodiment, in compounds (I)
$R^1$ is selected from $C_1$-$C_3$-alkyl,
$R^2$ is selected from branched $C_3$-$C_5$-alkyl, and
$R^3$ is $C_1$-$C_4$-alkyl,
where the total number of carbon atoms of the radicals $R^1$ and $R^2$ is in the range of from 6 to 7.

In another more specific embodiment, in compounds (I)
$R^1$ is selected from $C_1$-$C_3$-alkyl,
$R^2$ is selected from branched $C_4$-$C_6$-alkyl, and
$R^3$ is $C_1$-$C_4$-alkyl,
where the total number of carbon atoms of the radicals $R^1$ and $R^2$ is in the range of from 6 to 7.

In another specific embodiment, in compounds (I)
$R^1$ and $R^2$, independently of one another, are selected from methyl, ethyl and branched $C_3$-$C_6$-alkyl, and $R^3$ is selected from methyl or ethyl, in particular from ethyl, where the total number of carbon atoms of the radicals $R^1$ and $R^2$ is in the range of from 6 to 7.

In a more specific embodiment, in compounds (I)
$R^1$ is selected from $C_1$-$C_4$-alkyl,
$R^2$ is selected from branched $C_3$-$C_6$-alkyl,
$R^3$ is selected from methyl or ethyl, in particular from ethyl,
where the total number of carbon atoms of the radicals $R^1$ and $R^2$ is in the range of from 6 to 7.

In an even more specific embodiment, in compounds (I)
$R^1$ is selected from $C_1$-$C_3$-alkyl,
$R^2$ is selected from branched $C_3$-$C_5$-alkyl, and
$R^3$ is selected from methyl or ethyl, in particular from ethyl,
where the total number of carbon atoms of the radicals $R^1$ and $R^2$ is in the range of from 6 to 7.

In another even more specific embodiment, in compounds (I)
$R^1$ is selected from $C_1$-$C_3$-alkyl,
$R^2$ is selected from branched $C_4$-$C_6$-alkyl, and
$R^3$ is selected from methyl or ethyl, in particular from ethyl,
where the total number of carbon atoms of the radicals $R^1$ and $R^2$ is in the range of from 6 to 7.

In a special embodiment, in compounds (I)
$R^1$ is selected from methyl,
$R^2$ is selected from branched $C_5$-alkyl, and
$R^3$ is $C_1$-$C_4$-alkyl.

In another special embodiment, in compounds (I)
$R^1$ is selected from methyl,
$R^2$ is selected from branched $C_5$-alkyl, and
$R^3$ is selected from methyl or ethyl, in particular from ethyl.

It is further preferred that in the above mentioned embodiments, the branching in the radicals $R^2$ is located at least in the α- and/or the β-position to the attachment point of the radical $R^2$ to the rest of the molecule.

Due to their highly branched nature, the compounds (I) are often present in the form of isomer mixtures.

Thus, the present invention also relates to the use of a mixture of two or more compounds of the general formula (I), as defined herein, as an aroma chemical.

A preferred embodiment of the present invention relates the use of a mixture of two or more different compounds of the general formula (I) as defined above.

A more preferred embodiment of the present invention relates to the use of a mixture of two or more different compounds of the general formula (I)

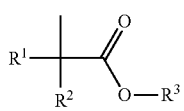
(I)

wherein
$R^1$ is selected from $C_1$-$C_3$-alkyl,
$R^2$ is selected from branched $C_3$-$C_5$-alkyl, and
$R^3$ is $C_1$-$C_4$-alkyl or $C_2$-$C_4$-alkenyl, preferably $C_1$-$C_4$-alkyl,
where the total number of carbon atoms of $R^1$ and $R^2$ is 6,
as an aroma chemical.

In this more preferred embodiment, $R^3$ in all compounds (I) present in the mixture preferably has the same meaning.

In this more preferred embodiment, $R^3$ is in particular methyl or ethyl. Specifically, $R^3$ is ethyl.

The amount of such compounds (I) in these mixtures is preferably at least 90% by weight, more preferably at least 95% by weight, even more preferably at least 98% by weight, in particular at least 99% by weight, based on the total weight of the mixture.

Examples of compounds that are typically present in the mixtures of this preferred embodiment are compounds of the formulae (I.1) to (I.5)

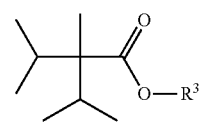
(I.1)

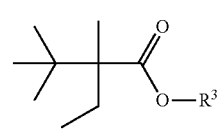
(I.2)

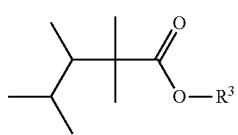
(I.3)

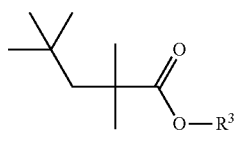
(I.4)

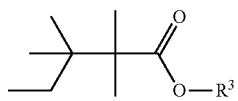
(I.5)

wherein $R^3$ has one of the meanings given above.

A particular embodiment of the present invention relates to the use of mixtures of compounds of the general formula (I)

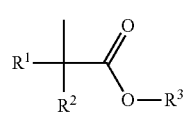
(I)

wherein
$R^1$ is selected from $C_1$-$C_3$-alkyl,
$R^2$ is selected from branched $C_3$-$C_5$-alkyl, and
$R^3$ is $C_1$-$C_4$-alkyl or $C_2$-$C_4$-alkenyl, preferably $C_1$-$C_4$-alkyl,
where the total number of carbon atoms of $R^1$ and $R^2$ is 6, comprising the compounds of the general formulae (I.1) to (I.5)

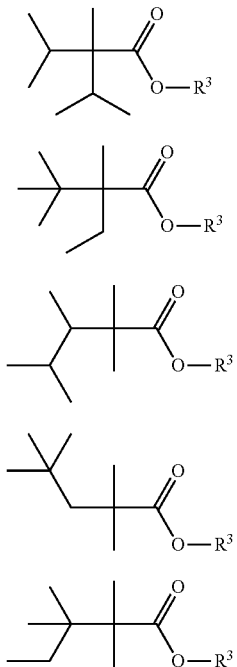

(I.1)
(I.2)
(I.3)
(I.4)
(I.5)

wherein R³ is $C_1$-$C_4$-alkyl or $C_2$-$C_4$-alkenyl, preferably $C_1$-$C_4$-alkyl, in particular ethyl, as an aroma chemical.

In this particular embodiment, R³ in all compounds (I.1) to (I.5) present in the mixture preferably has the same meaning.

The overall amount of the compounds (I.1), (I.2), (I.3), (I.4) and (I.5) in these mixtures is preferably at least 65% by weight, more preferably at least 80% by weight, even more preferably at least 90% by weight, in particular at least 95% by weight, based on the total weight of the mixture.

In this particular embodiment, specific mixtures are preferred, where in the compounds (I), (I.1), (I.2), (I.3), (I.4) and (I.5) R³ is selected from vinyl, and wherein the overall amount of the compounds (I.1), (I.2), (I.3), (I.4) and (I.5) in these mixtures is at least 90% by weight, based on the total weight of the mixture. These specific mixtures are hereinafter also referred to as "mixture A".

In this particular embodiment, specific mixtures are preferred, where in the compounds (I), (I.1), (I.2), (I.3), (I.4) and (I.5) R³ is selected from ethyl, and wherein the overall amount of the compounds (I.1), (I.2), (I.3), (I.4) and (I.5) in these mixtures is at least 90% by weight, based on the total weight of the mixture. These specific mixtures are hereinafter also referred to as "mixture B".

Another particular embodiment of the present invention relates to the use of mixtures of compounds of the general formula (I)

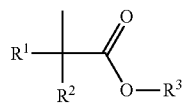

(I)

wherein
R¹ is selected from $C_1$-$C_3$-alkyl,
R² is selected from branched $C_3$-$C_5$-alkyl, and
R³ is $C_1$-$C_4$-alkyl or $C_2$-$C_4$-alkenyl, preferably $C_1$-$C_4$-alkyl,
where the total number of carbon atoms of R¹ and R² is 6, comprising the compounds of the general formulae (I.1) to (I.3)

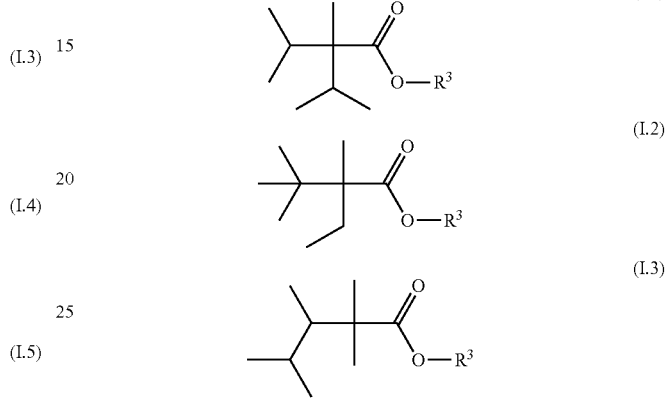

(I.1)
(I.2)
(I.3)

wherein R³ is $C_1$-$C_4$-alkyl, in particular ethyl, as an aroma chemical.

In this particular embodiment, R³ in all compounds (I.1) to (I.3) present in the mixture preferably has the same meaning.

The overall amount of the compounds (I.1), (I.2) and (I.3) in these mixtures is preferably at least 50% by weight, more preferably at least 75% by weight, even more preferably at least 85% by weight, in particular at least 90% by weight, based on the total weight of the mixture.

In this particular embodiment, specific mixtures are preferred, where in the compounds (I), (I.1), (I.2) and (I.3) R³ is selected from ethyl, and wherein the overall amount of the compounds (I.1), (I.2) and (I.3) in these mixtures is at least 85% by weight, based on the total weight of the mixture. These specific mixtures are hereinafter also referred to as "mixture C".

Another particular embodiment of the present invention relates to the use of mixtures of compounds of the general formula (I)

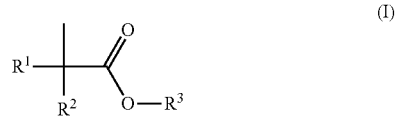

(I)

wherein
R¹ is selected from $C_1$-$C_3$-alkyl,
R² is selected from branched $C_3$-$C_5$-alkyl, and
R³ is $C_1$-$C_4$-alkyl or $C_2$-$C_4$-alkenyl, preferably $C_1$-$C_4$-alkyl,
where the total number of carbon atoms of R¹ and R² is 6, comprising the compound of the general formula (I.4)

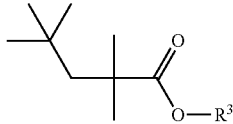
(I.4)

wherein $R^3$ is $C_1$-$C_4$-alkyl, in particular ethyl,
as an aroma chemical.

The amount of the compound (I.4) in these mixtures is preferably at least 10% by weight, more preferably at least 50% by weight, even more preferably at least 70% by weight, in particular at least 80% by weight, especially at least 85% by weight, based on the total weight of the mixture.

In this particular embodiment, specific mixtures are preferred, where in the compounds (I) and (I.4) $R^3$ is selected from ethyl, and wherein the amount of the compound (I.4) in these mixtures is at least 80% by weight, based on the total weight of the mixture. These specific mixtures are hereinafter also referred to as "mixture D".

Another particular embodiment of the present invention relates to the use of mixtures of compounds of the general formula (I)

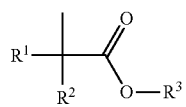
(I)

wherein
$R^1$ is selected from $C_1$-$C_3$-alkyl,
$R^2$ is selected from branched $C_3$-$C_5$-alkyl, and
$R^3$ is $C_1$-$C_4$-alkyl or $C_2$-$C_4$-alkenyl, preferably $C_1$-$C_4$-alkyl,
where the total number of carbon atoms of $R^1$ and $R^2$ is 6,
comprising the compound of the general formula (I.5)

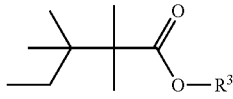
(I.5)

wherein $R^3$ is $C_1$-$C_4$-alkyl, in particular ethyl,
as an aroma chemical.

The amount of the compound (I.5) in these mixtures is preferably at least 10% by weight, more preferably at least 50% by weight, even more preferably at least 75% by weight, in particular at least 85% by weight, especially at least 90% by weight, based on the total weight of the mixture.

In this particular embodiment, specific mixtures are preferred, where in the compounds (I) and (I.5) $R^3$ is selected from ethyl, and wherein the amount of the compound (I.5) in these mixtures is at least 85% by weight, based on the total weight of the mixture. These specific mixtures are hereinafter also referred to as "mixture E".

Another preferred embodiment of the present invention relates the use of a mixture of two or more different compounds of the general formula (I)

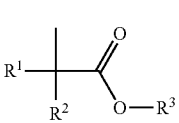
(I)

wherein
$R^1$ is selected from $C_1$-$C_4$-alkyl,
$R^2$ is selected from branched $C_3$-$C_6$-alkyl, and
$R^3$ is $C_1$-$C_4$-alkyl or $C_2$-$C_4$-alkenyl, preferably $C_1$-$C_4$-alkyl,
where the total number of carbon atoms of $R^1$ and $R^2$ is 7, as an aroma chemical.

The amount of the compounds (I) in these mixtures is preferably at least 90% by weight, more preferably at least 95% by weight, even more preferably at least 98% by weight, in particular at least 99% by weight, on the total weight of the mixture.

Examples of compounds that are typically present in the mixtures of this preferred embodiment are compounds of the formulae (I.8) to (I.16)

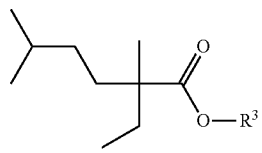
(I.8)

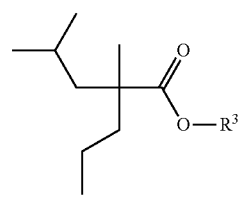
(I.9)

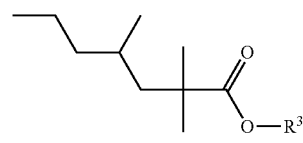
(I.10)

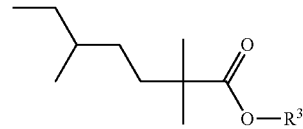
(I.11)

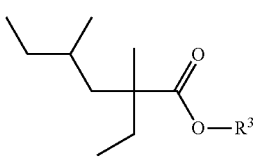
(I.12)

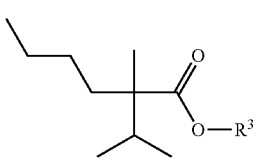
(I.13)

-continued

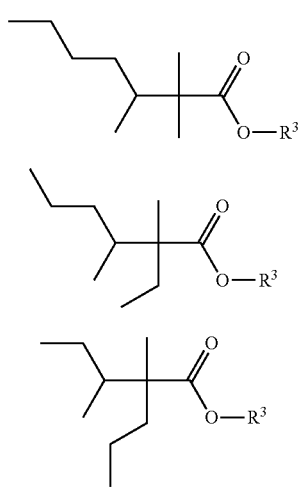

(I.14)

(I.15)

(I.16)

In this preferred embodiment, $R^3$ is in particular methyl or ethyl. Specifically, $R^3$ is ethyl.

Another more preferred embodiment of the present invention relates to the use of mixtures of compounds of the general formula (I)

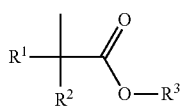

(I)

wherein
$R^1$ is selected from $C_1$-$C_4$-alkyl,
$R^2$ is selected from branched $C_3$-$C_6$-alkyl, and
$R^3$ is $C_1$-$C_4$-alkyl or $C_2$-$C_4$-alkenyl, preferably $C_1$-$C_4$-alkyl,
where the total number of carbon atoms of $R^1$ and $R^2$ is 7,
comprising the compounds of the general formulae (I.8) to (I.12)

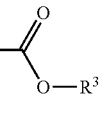

(I.8)

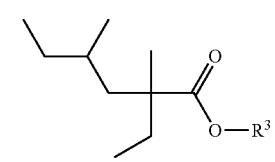

(I.9)

(I.10)

(I.11)

(I.12)

wherein $R^3$ is $C_1$-$C_4$-alkyl, in particular ethyl,
as an aroma chemical.

The overall amount of the compounds (I.8), (I.9), (I.10), (I.11) and (I.12) in these mixtures is preferably at least 50% by weight, more preferably at least 60% by weight, even more preferably at least 65% by weight, in particular at least 70% by weight, based on the total weight of the mixture.

Another more preferred embodiment of the present invention relates to the use of mixtures of compounds of the general formula (I)

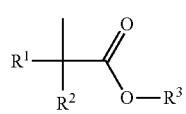

(I)

wherein
$R^1$ is selected from $C_1$-$C_4$-alkyl,
$R^2$ is selected from branched $C_3$-$C_6$-alkyl, and
$R^3$ is $C_1$-$C_4$-alkyl or $C_2$-$C_4$-alkenyl, preferably $C_1$-$C_4$-alkyl,
where the total number of carbon atoms of $R^1$ and $R^2$ is 7,
comprising the compounds of the general formulae (I.3) to (I.16)

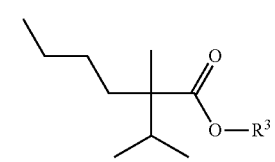

(I.13)

(I.14)

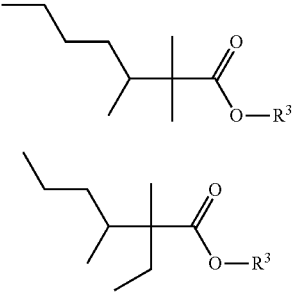

(I.15)

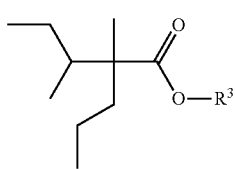

(I.16)

wherein $R^3$ is $C_1$-$C_4$-alkyl, in particular ethyl, as an aroma chemical.

The overall amount of the compounds (I.8), (I.9), (I.10), (I.11) and (I.12) in these mixtures is preferably at least 50% by weight, more preferably at least 55% by weight, in particular at least 60% by weight, based on the total weight of the mixture.

A particular embodiment of the present invention relates the use of a mixture of 4 or more different compounds of the general formula (I.6)

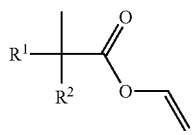

(I.6)

wherein
$R^1$ is selected from $C_1$-$C_3$-alkyl, and
$R^2$ is selected from branched $C_4$-$C_6$-alkyl,
where the total number of carbon atoms of $R^1$ and $R^2$ is 7,
as an aroma chemical.

The overall amount of the compounds (I.6) in these mixtures is preferably at least 50% by weight, more preferably at least 70% by weight, even more preferably at least 80% by weight, in particular at least 90% by weight, on the total weight of the mixture.

The mixtures of this particular embodiment are hereinafter also referred to as "mixture F".

Another particular embodiment of the present invention relates the use of a mixture of 10 or more different compounds of the general formula (I.6)

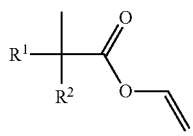

(I.6)

wherein
$R^1$ is selected from $C_1$-$C_3$-alkyl, and
$R^2$ is selected from branched $C_4$-$C_6$-alkyl,
where the total number of carbon atoms of $R^1$ and $R^2$ is 7, as an aroma chemical.

The overall amount of the compounds (I.6) in these mixtures is preferably at least 70% by weight, more preferably at least 80% by weight, even more preferably at least 90% by weight, in particular at least 95% by weight, on the total weight of the mixture.

Another particular embodiment of the present invention relates the use of a mixture of 10 or more different compounds of the general formula (I.7)

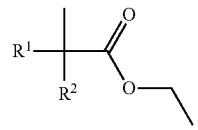

(I.7)

wherein
$R^1$ is selected from $C_1$-$C_3$-alkyl, and
$R^2$ is selected from branched $C_4$-$C_6$-alkyl,
where the total number of carbon atoms of $R^1$ and $R^2$ is 7,
as an aroma chemical.

The overall amount of the compounds (I.7) in these mixtures is preferably at least 70% by weight, more preferably at least 80% by weight, even more preferably at least 90% by weight, in particular at least 95% by weight, on the total weight of the mixture.

Another particular embodiment of the present invention relates the use of a mixture of 4 or more different compounds of the general formula (I.7)

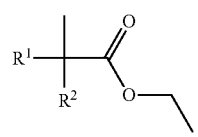

(I.7)

wherein
$R^1$ is selected from $C_1$-$C_3$-alkyl, and
$R^2$ is selected from branched $C_4$-$C_6$-alkyl,
where the total number of carbon atoms of $R^1$ and $R^2$ is 7,
as an aroma chemical.

The overall amount of the compounds (I.7) in these mixtures is preferably at least 50% by weight, more preferably at least 70% by weight, even more preferably at least 80% by weight, in particular at least 90% by weight, on the total weight of the mixture.

The mixtures of this particular embodiment are hereinafter also referred to as "mixture G".

Another embodiment of the present invention relates the use of a compound of the general formula (I)

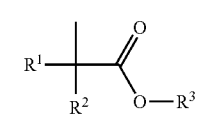

(I)

wherein
$R^1$ is $C_1$-$C_4$-alkyl,
$R^2$ is branched $C_3$-$C_6$-alkyl, and
$R^3$ is $C_1$-$C_4$-alkyl or $C_2$-$C_4$-alkenyl,
where the total number of carbon atoms of the radicals $R^1$ and $R^2$ is in the range of from 4 to 7,
or of a stereoisomer thereof or of a mixture of two or more stereoisomers thereof.

In this embodiment, it is further preferred that the branching in the radicals $R^2$ is located at least in the α- and/or the β-position to the attachment point of the radical $R^2$ to the rest of the molecule.

The compounds of formula (I) as well as the mixtures of two or more compounds of formula (I), the stereoisomers thereof and the mixtures of stereoisomers thereof, as defined above, are useful as aroma chemicals.

The term "aroma chemical" denotes a substance which is used to obtain a sensory impression, to be more precise an olfactory or flavor impression, in particular a fragrance or flavor impression. The term "olfactory" denotes an odor impression without any positive or negative judgement, while the term "fragrance" (also termed "perfume" or "scent") is connected to an odor impression which is generally felt as pleasant. A flavor induces a taste impression.

"Pleasant odor", "pleasant odor impression", "pleasant odiferous properties", "odor impression felt as pleasant" and similar terms are hedonistic expressions which describe the niceness and conciseness of an odor impression conveyed by an aroma chemical.

The more general hedonistic expressions "advantageous sensory properties" or "advantageous organoleptic properties" describe the niceness and conciseness of an organoleptic impression conveyed by an aroma chemical. In terms of the present invention, the terms "organoleptic" and "sensory" relate to olfactory or flavor properties. "Niceness" and "conciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

The term "odor-intensive substances" refers to substances or aroma chemicals exhibiting intense odor impressions. Intense odor impressions are to be understood as meaning those properties of aroma chemicals which permit a striking perception even in very low gas space concentrations. The intensity can be determined via a threshold value determination. A threshold value is the concentration of a substance in the relevant gas space at which an odor impression can just still be perceived by a representative test panel, although it no longer has to be defined. A substance class which probably belongs to the most odor-intensive known substance classes, i.e. has very low odor threshold values, are thiols, whose threshold value is often in the ppb/m$^3$ range.

Preferably, the compound of formula (I) or a mixture of two or more compounds of formula (I), or a stereoisomer thereof or a mixture of stereoisomers thereof as defined above is used for imparting an olfactory impression. In particular, the compounds of formula (I) as well as the mixtures of two or more compounds of formula (I), the stereoisomers thereof and the mixtures of stereoisomers thereof, as defined above, are used as a fragrance.

In particular, the "mixture A", as described above, is used to impart a fresh, fruity, sweet and woody note; or are used to produce a scent with a fresh, fruity, sweet and woody note.

In particular, the "mixture B", as described above, is used to impart a fruity, apple, damascone, blue berry, eucalyptus, camphor and rum note; or are used to produce a scent with a fruity, apple, damascone, blue berry, eucalyptus, camphor and rum note.

In particular, the "mixture C", as described above, is used to impart a sweet, woody, dried fruit, spicy and ethereal note; or are used to produce a scent with a sweet, woody, dried fruit, spicy and ethereal note.

In particular, the "mixture D", as described above, is used to impart an earthy, yeasty, blue berry, sweet and slightly moldy note; or are used to produce a scent with an earthy, yeasty, blue berry, sweet and slightly moldy note.

In particular, the "mixture E", as described above, is used to impart a woody, sweet, spicy and clove note; or are used to produce a scent with a woody, sweet, spicy and clove note.

In particular, the "mixture F", as described above, is used to impart a dried fruit, fruity, sweet, floral and violet note; or are used to produce a scent with a dried fruit, fruity, sweet, floral and violet note.

In particular, the "mixture G", as described above, is used to impart a sweet, fruity, red berries, herbal and tea; or are used to produce a scent with a sweet, fruity, red berries, herbal and tea note.

In particular, the "mixture H", of example 1.8, is used to impart a red berry, blueberry, cedarwood, dried fruit, sweet and minty note; or are used to produce a scent with a red berry, blueberry, cedarwood, dried fruit, sweet and minty note.

In particular, the "mixture I", of example 1.9, is used to impart a red berry, minty and dried fruit note; or are used to produce a scent with red berry, minty and dried fruit note.

In particular, the "mixture J", of example 1.10, is used to impart a blueberry, cedarwood, sweet and ethereal note; or are used to produce a scent with blueberry, cedarwood, sweet and ethereal note.

The compounds of formula (I) as well as the mixtures of two or more compounds of formula (I), the stereoisomers thereof and the mixtures of stereoisomers thereof, as defined above, are generally used in a ready-to-use composition, in particular in a fragranced ready-to-use composition. "Fragranced ready-to-use composition", as used herein, refers to a ready-to-use composition which predominately induces a pleasant odor impression.

Fragranced ready-to-use compositions are for example compositions used in personal care, in home care, in industrial applications as well as compositions used in other applications, such as pharmaceutical compositions or crop protection compositions.

Preferably, the compounds of formula (I) as well as the mixtures of two or more compounds of formula (I), the stereoisomers thereof and the mixtures of stereoisomers thereof are used in a composition selected from the group consisting of perfume compositions, body care compositions (including cosmetic compositions and products for oral and dental hygiene), hygiene articles, cleaning compositions (including dishwashing compositions), textile detergent compositions, compositions for scent dispensers, foods, food supplements, pharmaceutical compositions and crop protection compositions. The compounds of formula (I) as well as the mixtures of two or more compounds of formula (I), the stereoisomers thereof and the mixtures of stereoisomers thereof are used as an aroma chemical, preferably as a fragrance, in the above compositions.

In particular, the above "mixture A" is used to impart a fresh, fruity, sweet and woody note to the above-listed compositions.

In particular, the above "mixture B" is used to impart a fruity, apple, damascone, blue berry, eucalyptus, camphor and rum note to the above-listed compositions.

In particular, the above "mixture C" is used to impart a sweet, woody, dried fruit, spicy and ethereal note to the above-listed compositions.

In particular, the above "mixture D" is used to impart an earthy, yeasty, blue berry, sweet and slightly moldy note to the above-listed compositions.

In particular, the above "mixture E" is used to impart a woody, sweet, spicy and clove note to the above-listed compositions.

In particular, the above "mixture F" is used to impart a dried fruit, fruity, sweet, floral and violet note to the above-listed compositions.

In particular, the above "mixture G" is used to impart a sweet, fruity, red berries, herbal and tea note to the above-listed compositions.

In particular, the "mixture H" of example 1.8 is used to impart a red berry, blueberry, cedarwood, dried fruit, sweet and minty note to the above-listed compositions.

In particular, the "mixture I" of example 1.9 is used to impart a red berry, minty and dried fruit note to the above-listed compositions.

In particular, the "mixture J" of example 1.10 is used to impart a blueberry, cedarwood, sweet and ethereal note to the above-listed compositions.

Details to the above-listed compositions are given below.

In addition to the olfactory properties, the compounds of formula (I) as well as the mixtures of two or more compounds of formula (I), the stereoisomers thereof and the mixtures of stereoisomers thereof exhibit advantageous secondary properties.

For example, they can provide better sensory profiles as a result of synergistic effects with other fragrances, which means that they can provide a booster effect for other fragrances. They are therefore suitable as boosters for other fragrances.

Accordingly, another aspect of the invention relates to the use of a compounds of formula (I) or mixtures of two or more compounds of formula (I), or a stereoisomer thereof or a mixtures of stereoisomers thereof for modifying the scent character of a fragranced composition; and specifically to the use as a booster for other fragrances.

Booster effect means that the substances enhance and intensify in perfumery formulations the overall impression of the mixture. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all. In fragrance applications, Hedione® (methyl dihydrojasmonate), which as a pure substance only exhibits a light floral jasmin-note, reinforces diffusion, freshness and volume of a perfume composition as an odor booster. Booster effects are particularly desired when top-note-characterized applications are required, in which the odor impression is to be conveyed particularly quickly and intensively, for example in deodorants, air fresheners or in the taste sector in chewing gums.

To achieve such a booster effect, the compounds of formula (I) or the mixture of two or more compounds of formula (I), or the stereoisomers thereof or the mixtures of stereoisomers thereof are generally used in an overall amount of 0.1 to 20% by weight, preferably in an amount of 0.5 to 5% by weight, in particular in an amount of from 0.6 to 3% by weight, based on the total weight of the fragrance mixture.

Furthermore, the compounds of formula (I) as well as the mixtures of two or more compounds of formula (I), the stereoisomers thereof and the mixtures of stereoisomers thereof can have further positive effects on the composition in which they are used. For example, they can enhance the overall performance of the composition into which they are incorporated, such as the stability, e.g. the formulation stability, the extendability or the staying power of the composition.

In another aspect, the present invention relates to an aroma chemical composition comprising the compounds of formula (I) or a mixture of two or more compounds of formula (I), or a stereoisomer thereof or a mixture of stereoisomers thereof. The term "aroma chemical composition", as used herein, refers to a composition which induces a pleasant odor impression.

Preferably, the aroma chemical composition comprises
a compound of formula (I) or a mixture of two or more compounds of the general formula (I) or a stereoisomer thereof or a mixture of two or more stereoisomers thereof; and
at least one further aroma chemical and/or a non-aroma chemical carrier, where the non-aroma chemical carrier is in particular selected from the group consisting of surfactants, oil components (emollients) and solvents.

The further aroma chemical is of course different from the compounds of formula (I) or its stereoisomers or mixtures of its stereoisomers.

By virtue of their physical properties, the compounds of formula (I) as well as the mixtures of two or more compounds of formula (I), the stereoisomers thereof and the mixtures of stereoisomers thereof have particularly good, virtually universal solvent properties for other fragrances and other customary ingredients in fragranced ready to use compositions such as, in particular, perfume compositions. Therefore, they are well combinable with other aroma chemicals, allowing, in particular, the creation of perfume compositions having novel advantageous sensory profiles. Especially, as already explained above, they can provide a booster effect for other fragrances.

Accordingly, in one preferred embodiment, the aroma chemical composition comprises a compound of formula (I) or a mixture of two or more compounds of formula (I), a stereoisomer thereof or a mixture of stereoisomers thereof, as defined above; and at least one further aroma chemical.

The further aroma chemical can for example be one, preferably 2, 3, 4, 5, 6, 7, 8 or further aroma chemicals, selected from the group consisting of:

Geranyl acetate (3,7-Dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydro-cyclopenta[g]benzopyran (Galaxolid[3]), tetrahydrolinalool (3,7-dimethyloctan-3-ol), ethyl-linalool, benzyl salicylate, 2-methyl-3-(4-tert-butylphenyl)propanal (Lysmeral[2a]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorat[1]), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitral[1]), 2,4,4,7-tetramethyloct-6-en-3-one (Claritone[1]), 2,6-dimethyl-5-hepten-1-al (Melonal[2]), borneol, 3-(3-isopropylphenyl) butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70% by weight) or more and 2,5,5-trimethyl-1,2,3,4,4a,5,6,7-octahydronaphthalen-2-ol (Ambrinol S[1]). Within the context of the present invention, the aforementioned aroma chemical(s) are accordingly preferably combined with the compound of formula (I) or a mixture of two or more compounds of formula (I), or a mixture of stereoisomers thereof or a double bond isomer thereof, as defined above.

A further embodiment of the invention relates to a composition comprising the compound of formula (I) or a mixture of two or more compounds of formula (I), or a stereoisomer thereof or a mixture of stereoisomers thereof, as defined above, and at least one further aroma chemical selected from the group consisting of methyl benzoate, benzyl acetate, geranyl acetate, 2-isobutyl-4-methyltetrahydro-2H-pyran-4-ol and linalool.

A further embodiment of the invention relates to a composition comprising the compound of formula (I) or a mixture of two or more compounds of formula (I), or a stereoisomer thereof or a mixture of stereoisomers thereof, as defined above, and 2-isobutyl-4-methyltetrahydro-2H-pyran-4-ol.

A further embodiment of the invention relates to a composition comprising the compound of formula (I) or a mixture of two or more compounds of formula (I), or a stereoisomer thereof or a mixture of stereoisomers thereof, as defined above, and methyl benzoate.

Where trade names are given above, these refer to the following sources:

[1] trade name of Symrise GmbH, Germany;
[2] trade name of Givaudan AG, Switzerland;
[2a] trade name of BASF SE, Germany;
[3] trade name of International Flavors & Fragrances Inc., USA;
[5] trade name of Danisco Seillans S.A., France;
[9] trade name of Firmenich S.A., Switzerland;
[10] trade name of PFW Aroma Chemicals B.V., the Netherlands.

Further aroma chemicals with which the compound of formula (I) or a mixture of two or more compounds of formula (I), or a stereoisomer thereof or a mixture of stereoisomers thereof, as defined above, can be combined, e.g. to give a composition according to the invention, can be found e.g. in S. Arctander, Perfume and Flavor Chemicals, Vol. I and II, Montclair, N.J., 1969, self-published or K. Bauer, D. Garbe and H. Surburg, Common Fragrance and Flavor Materials, 4th Ed., Wiley-VCH, Weinheim 2001. Specifically, mention may be made of:

extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; eucalyptus citriodora oil; eucalyptus oil; fennel oil; pine needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calmus oil; camomile oil blue; roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; litsea cubeba oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolubalsam; tonka absolute; tuberose absolute; vanilla extract; violet leaf absolute; verbena oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1- methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethyl-acetals of geranial, neral, 7-hydroxy-3,7-dimethyloctanal;

the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol;

2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclo-hexadecen-1-one; 7-cyclohexadecen-1-one; (7/8)-cyclohexadecen-1-one; 9-cyclo-heptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)-ethanone; 2-benzofuranylethanone; (3-methyl-2-benzofuranyl)ethanone; benzo-phenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl) propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Advantageous are combinations with aroma chemicals with a sweet note, such as vanillin, 2,5-dimethyl-4-hydroxy-2H-furan-3-one (furaneol) or 3-hydroxy-2-methyl-4H-pyran-4-one (maltol), of the sweet note of which is boosted by the compound (1) or by a mixture of two or more compounds (1), or its stereoisomers or mixtures of its stereoisomers.

A further aspect of the invention is directed to a composition comprising the compound of formula (I) or a mixture of two or more compounds of formula (I), or a stereoisomer thereof or a mixture of stereoisomers thereof, as defined above, and at least one component selected from the group consisting of surfactants, emollients (oil component) and solvents.

One embodiment of the invention is directed to a composition comprising the compound of formula (I) or a mixture of two or more compounds of formula (I), or a stereoisomer thereof or a mixture of stereoisomers thereof, as defined above, and at least one solvent.

In the context of the present invention, a "solvent" serves for the dilution of the compound of formula (I) or a mixture of two or more compounds of formula (I), or a stereoisomer thereof or a mixture of stereoisomers thereof, as defined above, to be used according to the invention without having its own odiferous properties. Some solvents have fixing properties at the same time.

The one or more solvent(s) can be present in the composition from 0.01 to 99% by weight based on the composition. In a preferred embodiment of the invention, the composition comprise 0.1 to 90 weight %, preferably 0.5 to 80 weight % of solvent(s) based on the composition. The amount of solvent(s) can be chosen depending on the composition. In one embodiment of the invention, the composition comprises 0.05 to 10 weight %, preferably 0.1 to 5 weight %, more preferably 0.2 to 3 weight % based on the composition. In one embodiment of the invention, the composition comprises 20 to 70 weight %, preferably 25 to 50 weight % of solvent(s) based on the composition.

Preferred solvents are ethanol, propanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further aspect, the compounds of formula (I) as well as the mixtures of two or more compounds of formula (I), the stereoisomers thereof and the mixtures of stereoisomers thereof are suitable for use in surfactant-containing compositions. According to their characteristic scent profiles, they can especially be used for the perfuming of surfactant-containing compositions such as, for example, cleaners (in particular laundry care products and all-purpose cleaners).

One embodiment of the invention is therefore directed to a composition comprising the compound of formula (I) or a mixture of two or more compounds of formula (I), or a stereoisomer thereof or a mixture of stereoisomers thereof, as defined above, and at least one surfactant.

The surfactant(s) may be selected from anionic, nonionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in a quantity of 0 to 40% by weight, preferably 0 to 20% by weight, more preferably 0.1 to 15% by weight, and particularly 0.1 to 10% by weight, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one $—COO^{(-)}$ or $—SO_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_8$ to $C_{18}$ alkyl or acyl group, contain at least one free amino group and at least one $—COOH—$ or $—SO_3H—$ group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalk-ylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear C12-8 alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trim ethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising the compound of formula (I) or a mixture of two or more compounds of formula (I), or a stereoisomer thereof or a mixture of stereoisomers thereof, as defined above, and at least one oil component.

The oil components are typically present in a total quantity of 0.1 to 80, preferably 0.5 to 70, more preferably 1 to 60, even more preferably 1 to 50% by weight, in particular 1 to 40% by weight, more particularly 5 to 25% by weight and specifically 5 to 15% by weight based on the composition.

The oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl ole-ate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkyl-hydroxycarboxylic acids with linear or branched $C_6$-$C_{22}$-fatty alcohols, more especially dioctyl malate, esters of linear and/or branched fatty acids with polyhydric alcohols (for example propylene glycol, dimer dial or trimer triol), triglycerides based on $C_6$-$C_{10}$-fatty acids, liquid mono-, di- and triglyceride mixtures based on $C_6$-$C_{18}$-fatty acids, esters of $C_6$-$C_{22}$-fatty alcohols and/or Guerbet alcohols with aromatic carboxylic acids, more particularly benzoic acid, esters of dicarboxylic acids with polyols containing 2 to 10 car-bon atoms and 2 to 6 hydroxyl groups, vegetable oils, branched primary alcohols, substituted cyclohexanes, linear and branched $C_6$-$C_{22}$-fatty alcohol carbonates such as, for example, dicaprylyl carbonate (Cetiol® CC), Guerbet carbonates based on fatty alcohols containing 6 to 18 and preferably 8 to 10 carbon atoms, esters of benzoic acid with linear and/or branched $C_6$ to $C_{22}$-alcohols (for example Finsolv® TN), linear or branched, symmetrical or non-symmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

The compounds of formula (I) as well as the mixtures of two or more compounds of formula (I), the stereoisomers thereof and the mixtures of stereoisomers thereof, as defined above, can be used in a wide range of aroma chemical compositions. The olfactory properties, the substance properties (such as solubility in customary solvents and compatibility with further customary constituents of such compositions), as well as the toxicological acceptability of the compounds of formula (I) as well as the mixtures of two or more compounds of formula (I), the stereoisomers thereof and the mixtures of stereoisomers thereof underline their particular suitability for the stated use purposes and compositions.

Suitable aroma chemical compositions are for example perfume compositions, body care compositions, products for oral and dental hygiene, hygiene articles, cleaning compositions, textile detergent compositions, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Parfum.

Body care compositions include cosmetic compositions and products for oral and dental hygiene, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hairsprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eye-shadows, nail varnishes, make-ups, lipsticks and mascara.

Products for oral and dental hygiene include toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing detergents both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the man-aging of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, anti-dandruff agents, anti-inflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, oils, waxes, fats, phospholipids, saturated fatty acids, mono- or polyunsaturated fatty acids, $\alpha$-hydroxy acids, polyhydroxy fatty acids, liquefiers, dyes, color-protection agents, pigments, anticorrosives, polyols, surfactants, electrolytes, organic solvents or silicone derivatives.

The compounds of formula (I) as well as the mixtures of two or more compounds of formula (I), the stereoisomers thereof and the mixtures of stereoisomers thereof, as defined above, as well as the aroma chemical compositions according to the invention comprising them can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the compounds of formula (I) or the mixtures of two or more compounds of formula (I), or the stereoisomers thereof or mixtures of stereoisomers thereof, as defined above, and composition obtainable by the above method of the invention, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting the compounds of formula (I) or the mixtures of two or more compounds of formula (I), or the stereoisomers thereof or mixtures of stereoisomers thereof, as defined above, or the composition obtainable by the above method of the invention with a suitable wax-like substance and by extrusion with subsequent solidification, optionally in a suitable solvent, e.g. isopropanol.

Generally, the total amount of the compounds of formula (I) or the mixtures of two or more compounds of formula (I), or the stereoisomers thereof or mixtures of stereoisomers thereof, in the aroma chemical compositions according to the present invention is typically adapted to the particular intended use or the intended application and can, thus, vary over a wide range. As a rule, the customary standard commercial amounts for scents are used.

The compositions according to the invention can comprise the compounds of formula (I) or the mixtures of two or more compounds of formula (I), or the stereoisomers thereof or mixtures of stereoisomers thereof, as defined above, in an overall amount of from 0.001 to 99.9% by weight, preferably from 0.01 to 90% by weight, more preferably from 0.05 to 80%, in particular from 0.1 to 60% by weight, more particularly from 0.1 to 40% by weight, e.g. from 0.1 to 10% by weight or 0.1 to 15% by weight, based on the total weight of the composition.

In one embodiment of the invention, the compositions comprise the compounds of formula (I) or the mixtures of two or more compounds of formula (I), or the stereoisomers thereof or mixtures of stereoisomers thereof, as defined above, in an overall amount of from 0.001 to 5 weight %, preferably from 0.01 to 2 weight % based on the total weight of the composition.

A further aspect of the invention is directed to a method of preparing an aroma chemical composition, in particular a fragranced composition, especially a fragranced ready-to-use composition, or for modifying the scent character of an aroma chemical composition, in particular of a fragranced composition, especially of a fragranced ready-to-use composition, comprising incorporating a compound of formula (I) or a mixture of two or more compounds of the general formula (I) or a stereoisomer thereof or a mixture of two or more stereoisomers thereof, as defined above, into the target composition, e.g. a ready-to-use composition. Alternatively, the invention is directed to a method of preparing an aroma chemical composition, in particular a fragranced composition, especially a fragranced ready-to-use composition, comprising mixing at least one compound of formula (I), a mixture of two or more compounds of the general formula (I), a stereoisomer thereof or a mixture of stereoisomers thereof with at least one aroma chemical different from compounds (I) and/or with at least one non-aroma chemical carrier. Suitable and preferred aroma chemicals different from compounds (I) and non-aroma chemical carriers are described above.

In particular, the invention is directed to a method of preparing a perfume composition, body care composition, product for oral and dental hygiene, hygiene article, cleaning composition, textile detergent composition, food, food supplement, pharmaceutical composition or crop protection composition, comprising including the compounds of formula (I), the stereoisomers thereof, the mixture of stereoisomers thereof or the double bond isomers thereof as defined above or in a perfume composition, body care composition, product for oral and dental hygiene, hygiene article, cleaning composition, textile detergent composition, food, food supplement, pharmaceutical composition or crop protection composition.

In one embodiment the invention is directed to a method for imparting a fresh, fruity, sweet and woody note to a perfume composition, body care composition, product for oral and dental hygiene, hygiene article, cleaning composition, textile detergent composition, food, food supplement, pharmaceutical composition or crop protection composition, which comprises including the "mixture A", as defined above, in a perfume composition, body care composition, product for oral and dental hygiene, hygiene article, cleaning composition, textile detergent composition, food, food supplement, pharmaceutical composition or crop protection composition.

In another embodiment the invention is directed to a method for imparting a fruity, apple, damascone, blue berry, eucalyptus, camphor and rum note to a perfume composition, body care composition, product for oral and dental hygiene, hygiene article, cleaning composition, textile detergent composition, food, food supplement, pharmaceutical composition or crop protection composition, which comprises including the "mixture B", as defined above, in a perfume composition, body care composition, product for oral and dental hygiene, hygiene article, cleaning composition, textile detergent composition, food, food supplement, pharmaceutical composition or crop protection composition.

In another embodiment the invention is directed to a method for imparting a sweet, woody, dried fruit, spicy and etherea note to a perfume composition, body care composition, product for oral and dental hygiene, hygiene article, cleaning composition, textile detergent composition, food, food supplement, pharmaceutical composition or crop protection composition, which comprises including the "mixture C", as defined above, in a perfume composition, body care composition, product for oral and dental hygiene, hygiene article, cleaning composition, textile detergent composition, food, food supplement, pharmaceutical composition or crop protection composition.

In another embodiment the invention is directed to a method for imparting a earthy, yeasty, blue berry, sweet and slightly moldy note to a perfume composition, body care composition, product for oral and dental hygiene, hygiene article, cleaning composition, textile detergent composition, food, food supplement, pharmaceutical composition or crop protection composition, which comprises including the "mixture D", as defined above, in a perfume composition, body care composition, product for oral and dental hygiene, hygiene article, cleaning composition, textile detergent composition, food, food supplement, pharmaceutical composition or crop protection composition.

In another embodiment the invention is directed to a method for imparting a woody, sweet, spicy and clove note to a perfume composition, body care composition, product for oral and dental hygiene, hygiene article, cleaning composition, textile detergent composition, food, food supplement, pharmaceutical composition or crop protection composition, which comprises including the "mixture E", as defined above, in a perfume composition, body care composition, product for oral and dental hygiene, hygiene article, cleaning composition, textile detergent composition, food, food supplement, pharmaceutical composition or crop protection composition.

In another embodiment the invention is directed to a method for imparting a dried fruit, fruity, sweet, floral and violet note to a perfume composition, body care composition, product for oral and dental hygiene, hygiene article, cleaning composition, textile detergent composition, food, food supplement, pharmaceutical composition or crop protection composition, which comprises including the "mixture F", as defined above, in a perfume composition, body care composition, product for oral and dental hygiene, hygiene article, cleaning composition, textile detergent composition, food, food supplement, pharmaceutical composition or crop protection composition.

In another embodiment the invention is directed to a method for imparting a sweet, fruity, red berries, herbal and tea note to a perfume composition, body care composition, products for oral and dental hygiene, hygiene article, cleaning composition, textile detergent composition, food, food supplement, pharmaceutical composition or crop protection composition, which comprises including the "mixture G", as defined herein, in a perfume composition, body care composition, hygiene article, cleaning composition, textile detergent composition, food, food supplement, pharmaceutical composition or crop protection composition.

In another embodiment the invention is directed to a method for imparting a red berry, blueberry, cedarwood, dried fruit, sweet, minty note to a perfume composition, body care composition, products for oral and dental hygiene, hygiene article, cleaning composition, textile detergent composition, food, food supplement, pharmaceutical composition or crop protection composition, which comprises including the "mixture H", as defined herein, in a perfume composition, body care composition, hygiene article, cleaning composition, textile detergent composition, food, food supplement, pharmaceutical composition or crop protection composition.

In another embodiment the invention is directed to a method for imparting a red berry, minty and dried fruit note to a perfume composition, body care composition, products for oral and dental hygiene, hygiene article, cleaning composition, textile detergent composition, food, food supplement, pharmaceutical composition or crop protection composition, which comprises including the "mixture I", as defined herein, in a perfume composition, body care composition, hygiene article, cleaning composition, textile detergent composition, food, food supplement, pharmaceutical composition or crop protection composition.

In another embodiment the invention is directed to a method for imparting a blueberry, cedarwood, sweet and ethereal note to a perfume composition, body care composition, products for oral and dental hygiene, hygiene article, cleaning composition, textile detergent composition, food, food supplement, pharmaceutical composition or crop protection composition, which comprises including the "mixture J", as defined herein, in a perfume composition, body care composition, hygiene article, cleaning composition, textile detergent composition, food, food supplement, pharmaceutical composition or crop protection composition.

In another aspect, the invention relates to a mixture of two or more different compounds of the general formula (I)

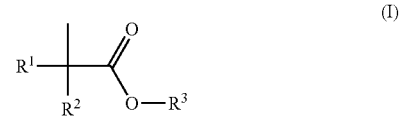

wherein
$R^1$ and $R^2$, independently of one another, are $C_1$-$C_8$-alkyl, and
$R^3$ is $C_1$-$C_4$-alkyl,
where the total number of carbon atoms of the radicals $R^1$ and $R^2$ is in the range of from 3 to 9.

As regards preferred meanings of the radicals $R^1$, $R^2$ and $R^3$ reference is made to the statements given above.

The term "a mixture of two or more stereoisomers thereof", as used herein, refers to any possible mixture of stereoisomers, and not only to mixtures comprising the maximum number of possible stereoisomers of a compound in the mixture. For example, for a compound containing two stereogenic centers, either one of the stereogenic centers may be present as R/S isomer mixture while the other stereogenic center is present in pure form, i.e. either as R or as S (mixture of 2 stereoisomers) or both stereogenic centers may be present as R/S isomer mixtures (mixture of 4 stereoisomers).

Preferably, the term "a mixture of two or more stereoisomers thereof" refers to mixtures comprising not all possible stereoisomers.

In another aspect, the invention relates to a mixture of two or more different compounds of the general formula (I)

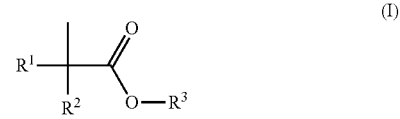

wherein
R¹ is selected from C₁-C₃-alkyl,
R² is selected from branched C₃-C₅-alkyl, and
R³ is C₁-C₄-alkyl,
where the total number of carbon atoms of R¹ and R² is 6.

In a preferred embodiment, in these compounds (I), R³ is selected from C₃-C₄-alkyl.

In another aspect, the invention relates to a mixture of two or more different compounds of the general formula (I)

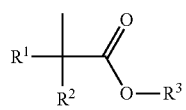
(I)

wherein
R¹ is selected from C₁-C₄-alkyl,
R² is selected from branched C₃-C₆-alkyl, and
R³ is C₁-C₄-alkyl,
where the total number of carbon atoms of R¹ and R² is 7.

Preferably, in these compounds (I),
R¹ is selected from C₁-C₃-alkyl, and
R² is selected from branched C₄-C₆-alkyl.

In a preferred embodiment, in these compounds (I), R³ is selected from C₃-C₄-alkyl.

In another aspect, the invention relates to a mixture comprising 4 or more different compounds of the general formulae (I.1) to (I.5)

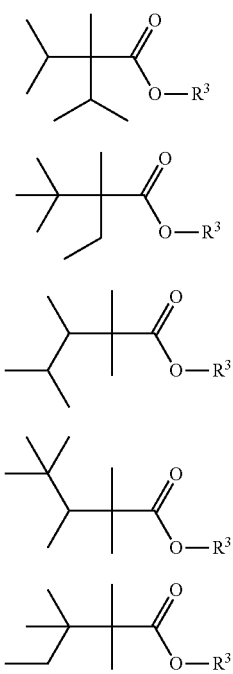

wherein R³ is C₁-C₄-alkyl, in particular ethyl.

In another aspect, the invention relates to a mixture comprising 4 or more different compounds of the general formulae (I.8) to (I.16)

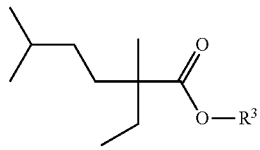
(I.8)

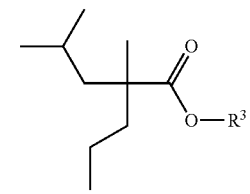
(I.9)

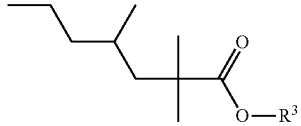
(I.10)

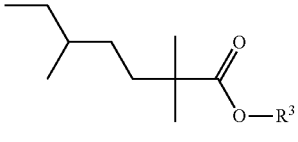
(I.11)

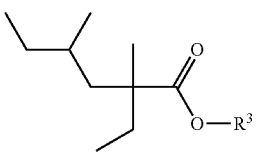
(I.12)

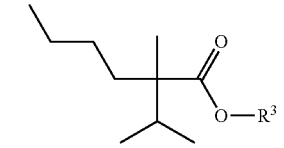
(I.13)

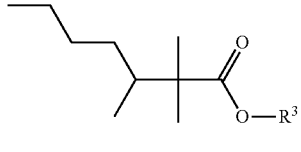
(I.14)

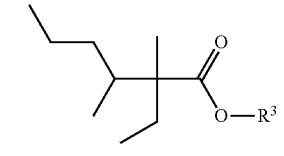
(I.15)

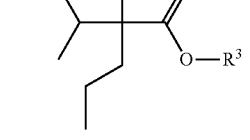
(I.16)

wherein R³ is C₁-C₄-alkyl, in particular ethyl.

The compounds of the formula (I) can be prepared by standard methods of organic chemistry.

To be more precise, the compounds (I) can efficiently be prepared for example by reacting a carboxylic acid or a carboxylic acid chloride of the general formula (II.a) or (II.b)

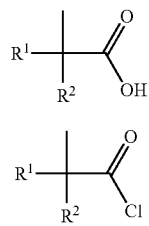

wherein $R^1$ and $R^2$ have one of the meanings given above, with an alcohol $R^3$—OH, wherein $R^3$ has one of the meanings given above. In case a carboxylic acid of formula (II.a) is applied, the reaction is typically performed in the presence of an esterification catalyst. In case a carboxylic acid chloride of formula (II.b) is applied, the reaction is typically performed in the presence of a base.

Suitable bases are preferably selected from organic bases. Suitable organic bases that can be used are for example tertiary amines, e.g. trimethylamine, triethylamine, tripropylamine, ethyldiisopropylamine and the like, or basic N-heterocycles, such as morpholine, pyridine, lutidine, DMAP, DABCO, DBU or DBN.

Suitable esterification catalysts that can be applied in this reaction are well known to the skilled person. Suitable esterification catalysts are for example metal based catalysts, e.g. iron, cadmium, cobalt, lead, zinc, antimony, magnesium, titanium and tin catalysts in the form of metals, metal oxides or metal salts, such as metal alcoxylates; mineral acids, such as sulfuric acid, hydrochloric acid or phosphoric acid; or organic sulfonic acids, such as methane sulfonic acid or para-toluene sulfonic acid.

The individual reaction conditions for the preparation of the ester compounds of the general formula (I) are well known to the skilled person.

Alternatively, the ester compounds of the general formula (I) can be prepared by reacting the carboxylic acid of formula (II.a) with an alkylation reagent $R^3$—X, wherein $R^3$ has one of the meanings given above and X represents a leaving group, selected from halogen, such as Cl, Br, I, and sulfonates, such as tosylate, mesylate, triflate or nonaflate, typically in the presence of a base.

Suitable bases are typically selected from inorganic bases and organic bases.

Suitable inorganic bases that can be used in this alkylation reaction are for example alkali metal carbonates, e.g. $Li_2CO_3$, $Na_2CO_3$, $K_2CO_3$ or $Cs_2CO_3$, alkali metal hydroxides, e.g. LiOH, NaOH or KOH, and hydride donors, e.g. NaH, $LiAlH_4$ or $NaBH_4$.

Suitable organic bases that can be used in this alkylation reaction are for example tertiary amines, e.g. trimethylamine, triethylamine, tripropylamine, ethyldiisopropylamine and the like, or basic N-heterocycles, such as morpholine, pyridine, lutidine, DMAP, DABCO, DBU or DBN.

The alkylation reaction is performed under conventional alkylation reaction conditions that are well known to the skilled person.

Alternatively, the compounds of formula (I), wherein $R^3$ is selected from $C_2$-$C_4$-alkyl, can also be prepared by catalytic hydrogenation of the corresponding compounds of formula (I), wherein $R^3$ is selected from $C_2$-$C_4$-alkenyl.

Accordingly, the present invention further relates to a process for the production of compounds of formula (I) wherein
$R^1$ and $R^2$, independently of one another, are $C_1$-$C_8$-alkyl, and
$R^3$ is selected from $C_2$-$C_4$-alkyl,
where the total number of carbon atoms of the radicals $R^1$ and $R^2$ is in the range of from 3 to 9,
or of a mixture of two or more compounds of the general formula (I),
or of a stereoisomer thereof or of a mixture of two or more stereoisomers thereof,
comprising the following steps:
a) providing a compound of the general formula (I) wherein
$R^1$ and $R^2$, independently of one another, are $C_1$-$C_8$-alkyl, and
$R^3$ is selected from $C_2$-$C_4$-alkenyl,
where the total number of carbon atoms of the radicals $R^1$ and $R^2$ is in the range of from 3 to 9,
or of a mixture of two or more compounds of the general formula (I),
or of a stereoisomer thereof or of a mixture of two or more stereoisomers thereof,
b) subjecting the compound or the compound mixture provided in step a) to a catalytic hydrogenation reaction using hydrogen in the presence of a hydrogenation catalyst.

Suitable hydrogenation catalysts are those customarily used in the hydrogenation of olefinic carbon-carbon double bonds. The catalysts may be used either in heterogeneous phase or as homogeneous catalysts. Preferably, the catalysts are used in heterogeneous phase. The hydrogenation catalysts preferably comprise at least one metal of group VIII and also VIIa.

Suitable metals of group VIII are selected from the group consisting of ruthenium, cobalt, rhodium, nickel, palladium and platinum. A suitable metal of group VIIa is rhenium.

The metals may also be used in the form of mixtures. Metals of group VIII may also comprise small amounts of further metals, for example metals of group VIIa, in particular rhenium, or metals of group Ib, i.e. copper, silver or gold. Particularly suitable metals of group VIII are ruthenium, nickel, palladium and platinum. The catalyst especially comprises palladium as the catalytically active species.

When a heterogeneous catalyst is used, it can be present in finely divided form or in the form of larger molded bodies, such as strands or pellets. In case the heterogeneous catalyst is present in finely divided form, the finely divided form is achieved, for example, as follows:
a) Black catalyst: shortly before use as a catalyst, the metal is deposited reductively from the solution of one of its salts.
b) Adams catalyst: the metal oxides, in particular the oxides of platinum and palladium, are reduced in situ by the hydrogen used for the hydrogenation.
c) Skeletal or Raney catalyst: the catalyst is prepared as a "metal sponge" from a binary alloy of the metal (in particular nickel or cobalt) with aluminum or silicon by leaching out one partner with acid or alkali. Residues of the original alloy partner often act synergistically.
d) Supported catalyst: black catalysts can also be precipitated on the surface of a support substance. Suitable supports and support materials are described below.

The support material may be in the form of a fine powder but may also be used in the form of larger molded bodies, such as strands or pellets, in particular when the catalytic hydrogenation reaction is performed on industrial scales and/or continuously. The supports may consist of metallic or nonmetallic, porous or nonporous material. Suitable metallic materials are, for example, highly alloyed stainless steels. Suitable nonmetallic materials are, for example, mineral materials, for example natural and synthetic minerals, glasses or ceramics, plastics, for example synthetic or natural polymers, or a combination of the two. Preferred support materials are carbon, in particular activated carbon, silicon dioxide, in particular amorphous silicon dioxide, aluminumoxide ($Al_2O_3$), and also the sulfates and carbonates of the alkaline earth metals, calcium carbonate, calcium sulfate, magnesium carbonate, magnesium sulfate, barium carbonate and barium sulfate. In particular, the support material is selected from carbon and aluminumoxide ($Al_2O_3$).

The reaction temperature is generally from 30 to 200° C., preferably from 40 to 170° C., in particular from 50 to 150° C. The hydrogen pressure is generally from 1 to 100 bar absolute (0.1 to 10 MPa), preferably from 2 to 60 bar absolute (0.2 to 5 MPa), and in particular from 5 to 50 bar absolute (0.5 to 5 MPa). The hydrogenation can be carried out in a variety of reactors known for this purpose, such as a serial loop reactor as described in U.S. Pat. No. 5,756,856, but also in simpler reactors, as described for example in DE 2008128. Preference is given to fixed bed reactors, in particular to trickle bed reactors.

Typically, the crude product obtained in step b) is worked up by filtering off the catalyst and removing the solvent, if present, by distillation.

A preferred embodiment of the process relates to the process as defined above, where the process additionally comprises a purification step c), wherein the product obtained in step b) is subjected to a purification by distillation, in particular a purification by precision distillation.

The distillation in step c) is performed according to the methods known to the skilled person, preferably in an evaporator or in a distillation unit, comprising an evaporator and column(s) or a sequence of both. The distillation column(s) can be operated batchwise or continuously with column internals like trays, a structured packing or a random packing. The distillation is carried out at a maximum pressure of less than 200 mbar as measured at the column head, preferably less than 50 mbar. During start-up, the column is operated under total reflux and then the reflux ratio is adjusted to ≥2:1. Unreacted raw materials or solvents may be recycled back into the reaction.

An even more preferred embodiment of the above described process relates to a process for the production of a mixture of two or more different compounds of formula (I.7),

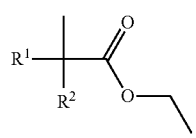

(I.7)

wherein
$R^1$ is selected from $C_1$-$C_3$-alkyl, and
$R^2$ is selected from branched $C_3$-$C_5$-alkyl,
where the total number of carbon atoms of the radicals $R^1$ and $R^2$ is 6, comprising the following steps:
a) providing a mixture of two or more different compounds of the general formula (I.6)

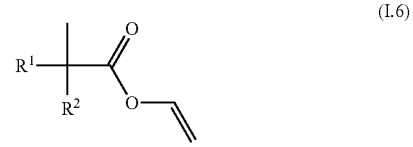

(I.6)

wherein
$R^1$ and $R^2$ are as defined above and where the total number of carbon atoms of the radicals $R^1$ and $R^2$ is 6,
b) subjecting the compound mixture provided in step a) to a catalytic hydrogenation reaction using hydrogen in the presence of a hydrogenation catalyst, and
c) subjecting the product mixture obtained in step b) to a purification by distillation, in particular a purification by precision distillation, to remove impurities having a boiling point that is lower than the boiling point of the compounds I.7 as defined above.

Also in thus preferred embodiment, the crude product obtained in step b) is typically worked up by filtering off the catalyst and removing the solvent, if present, by distillation.

Generally, the reaction mixtures are worked up in a customary manner, for example by filtering off the catalyst, if present, removing the solvent, if present, or by mixing with water, neutralizing, separating the phases, isolating the product from the organic phases and, if appropriate, purifying the crude products by usual methods, e.g. by distillative, extractive or chromatographic methods. If a heterogeneous catalyst is used for the reactions, e.g. a heterogeneous hydrogenation catalyst, the catalyst is filtered off prior to work up. Due to the highly branched nature of the carboxylic acid starting material the above reactions are often performed with mixtures of various region-isomers and/or optical isomers thereof. Consequently, the ester products are also often present as isomer mixtures in the resulting reaction mixtures. If desired, these can be separated from each other by customary means, such as distillative, extractive or chromatographic methods.

Generally, the carboxylic acids of formula (II), that are used as starting materials in the above described preparation processes, are readily available from commercial sources. Alternatively, the carboxylic acids of formula (II) can also by synthesized in large quantities using processes that are well described in the art.

The invention is illustrated by the following examples.

EXAMPLES

1. Preparation Examples

Abbreviations:
GC: Gas Chromatography
RT: retention time
Mixture A: Mixture of at least 5 isomers of the general formula (I.6), wherein
$R^1$ is selected from $C_1$-$C_3$-alkyl, and
$R^2$ is selected from branched $C_3$-$C_5$-alkyl,
where the total number of carbon atoms of $R^1$ and $R^2$ is 6,
which mixture comprises the compounds (I.1a) to (I.5a),

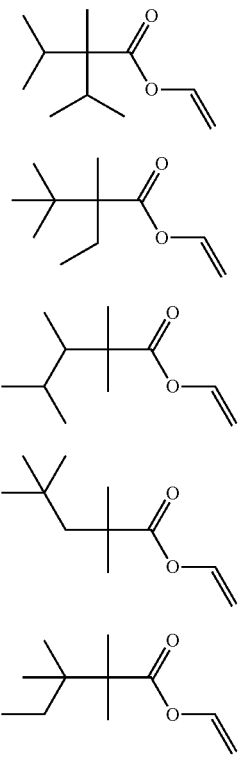

in the following amounts:

I.1a: 11-16% by weight,
I.2a+I.3a+I.4a: 65-70% by weight,
I.5a: 11-16% by weight,
based on the total weight of the mixture.

This mixture is commercially available from Hexion under the brand name VeoVa9. This mixture has the CAS-number 54423-67-5.

Mixture F: Mixture of at least 10 isomers of the general formula (I.6), wherein $R^1$ is selected from $C_1$-$C_4$-alkyl, and
$R^2$ is selected from branched $C_3$-$C_6$-alkyl,
where the total number of carbon atoms of $R^1$ and $R^2$ is 7.

This mixture is commercially available from Hexion under the brand name VeoVa10. This mixture has the CAS-number 51000-52-3.

Analytics:

The purity of the products was determined by gas chromatography on the basis of area-%:

Method for Mixtures A, B, C, D, E

GC column: CP-SIL (50 m (length), 0.32 mm (ID), 1.2 micrometer (film));

Temperature program: 3 min at 50° C., 50° C. to 180° C. at 4° C./min, 15 min at 230° C.;
Temperature of the injector: 250° C.;
Temperature of the detector: 300° C.;
Flow: 1.5 ml/min.

Method for Mixtures F, G, H, I J:

GC column: Rxi1 ms (30 m (length), 0.32 mm (ID), 0.5 micrometer (film));

Temperature program: 50° C. to 100° C. at 1° C./min, 20 min at 200° C.
Temperature of the injector: 250° C.;
Temperature of the detector 280° C.
Flow: 1.5 ml/min.

The products were identified by $^{13}C$ NMR.

1a) Preparation of Mixture B (in the Presence of Methanol and 5% Pd/C with 50% Water Content):

300 g of Mixture A were dissolved in 1.5 L of methanol. To this mixture 30 g of Pd/C (5% Pd on C with 50% water content) was added. The reaction vessel was connected to a gasburet filled with water. Then $H_2$ was pressed directly from the gas-bottle into the gasburet in a way that the $H_2$ consumption could be monitored. The reaction proceeded at RT and some exothermy was observed (max. temp 29.5° C.). The experiment was continued for 27 h and a 24.4 L consumption of $H_2$ was observed. The catalyst was filtered off and the solvent was evaporated at reduced pressure. 273.7 g of crude product were obtained. NMR confirmed full conversion since no traces of the unsaturated product were observed. A part of this crude reaction mixture (111.8 g) was subjected to distillative separation, only one major fraction was isolated. The olfactory properties of this major fraction were assessed (see Example 1.2 below).

1 b) Preparation of Mixture B (in the Presence of 5% Pd/C with 50% Water Content):

1500 g of Mixture A are placed in a 3.5 L stainless steel autoclave, previously inserted with nitrogen, together with 150 g of catalyst (5% Pd/C with 50% water content, in the form of a paste). While stirring at 700 rpm at ambient temperature, a hydrogen pressure of 15 bar is first applied. The reaction is then heated to 100° C. and the hydrogen pressure is increased to 30 bar. The reaction is maintained for 48 h at these reaction conditions, during which the hydrogen pressure is kept at 30 bar. The autoclave was then relaxed and cooled. The catalyst was filtered off and returned. The conversion rate to the reaction product (Mixture B) was determined via GC and iodine number. The conversion was >99.9%.

The crude reaction mixture was subjected to distillative separation (see example 1h).

1c) Preparation of Mixture B (in the Presence of Dried 5% Pd/C):

50 g of Mixture A are placed in a 270 ml stainless steel autoclave, previously inserted with nitrogen, together with 5 g of catalyst (5% Pd/C, dry). While stirring at 700 rpm at ambient temperature, a hydrogen pressure of 15 bar is first applied. The reaction is then heated to 120° C. and the hydrogen pressure is increased to 30 bar. The reaction is maintained for 24 h at these reaction conditions, during which the hydrogen pressure is kept at 30 bar. The autoclave was then relaxed and cooled. The catalyst was filtered off. The conversion rate to the reaction product (Mixture B) was determined via GC and iodine number. The conversion was >99.9%.

1d) Preparation of Mixture B (in the Presence of 0.25% Pd on $Al_2O_3$):

50 g of Mixture A are placed in a 270 ml stainless steel autoclave, previously inserted with nitrogen, together with 5 g of catalyst (0.25% Pd on aluminum oxide). While stirring at 700 rpm at ambient temperature, a hydrogen pressure of 15 bar is first applied. The reaction is then heated to 100° C. and the hydrogen pressure is increased to 30 bar. The reaction is maintained for 24 h at these reaction conditions, during which the hydrogen pressure is kept at 30 bar. The autoclave was then relaxed and cooled. The catalyst was filtered off. The conversion rate to the reaction product (Mixture B) was determined via GC and iodine number. The conversion was >99.8%.

1e) Preparation of Mixture B (in the Presence of Raney-Nickel):

50 g of Mixture A are placed in a 270 ml stainless steel autoclave, previously inserted with nitrogen, together with 2 g of catalyst (Raney-Nickel). While stirring at 700 rpm at ambient temperature, a hydrogen pressure of 15 bar is first applied. The reaction is then heated to 120° C. and the hydrogen pressure is increased to 30 bar. The reaction is maintained for 24 h at these reaction conditions, during which the hydrogen pressure is kept at 30 bar. The autoclave was then relaxed and cooled. The catalyst was filtered off. The conversion rate to the reaction product (Mixture B) was determined via GC. The conversion was >95%.

1f) Continuous Preparation of Mixture B:

Mixture A was hydrogenated in a continuous hydrogenation reaction in the presence of a aluminium oxide supported Pd catalyst (strands, 0.24% Pd). The continuous hydrogenation was carried out in an isothermal tube reactor at 100° C. and a hydrogen pressure of 30 bar. The volume of the catalyst was 190 ml, the load was 0.2 kg/Lcat*h (feed rate: 38 g/h). The feed to return ratio was 1:25, with a metered hydrogen quantity of 50 NL/h. The conversion rate to the reaction product (Mixture B) was determined via iodine number and was >99%.

1g) Preparation of Mixtures C, D and E:

The reaction from example 1a was repeated and 261.7 g of crude were subjected to a fine distillation using a 60 cm column with a 4 cm diameter. 59 cm of the column were filled with column packing (DN30 A3-1000 2.4610 8 27×50 mm). Two temperature measuring points were set at 18 cm and at 48 cm. The following fractions were isolated:

Fraction 5 contained 94% of a mixture of Compound I.2b (RT 29.59 min, 20-25%), Compound I.3b (RT 29.41 min, 40-45%) and Compound I.4b (RT 29.41 min, 10-20%). The olfactory properties of this mixture (Mixture C) were assessed (see Example 1.3 below). The corresponding structures were elucidated per NMR.

Compound I.2b

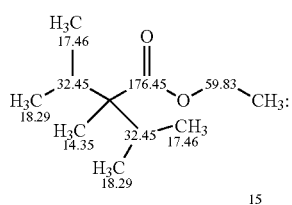

$^{13}$C NMR (125 MHz, CDCl$_3$): δ = 14.35, 14.20, 17.46, 18.29, 32.45, 52.41, 59.83, 176.45.

Compound I.3b

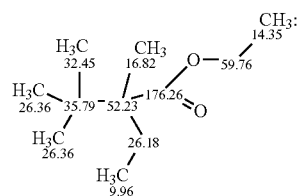

$^{13}$C NMR (125 MHz, CDCl$_3$): δ = 9.96, 14.35, 16.82, 26.18, 26.36, 32.45, 35.79, 52.23, 59.76, 176.26.

Compound I.4b

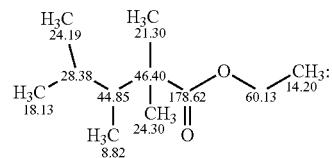

$^{13}$C NMR (125 MHz, CDCl$_3$): δ = 8.82, 14.20, 18.13, 21.30, 24.19, 24.30, 28.38, 44.85, 46.40, 60.13, 178.62

Fraction 1 contained 85% of Compound I.1b (RT 27.21 min). The olfactory properties of this mixture (Mixture D)

| Time min | Bottom T ° C. | Mes. 1 ° C. | Mes. 2 ° C. | Head T ° C. | Pressure mbar | Reflux ratio sec. | Fraction Nr. | Amount g |
|---|---|---|---|---|---|---|---|---|
| 20 | 69.9 | 62.5 | 55.8 | 52.2 | 0-1 | 99 to 2 | | |
| 60 | 70.5 | 61.3 | 51.3 | 46.9 | 0-1 | 99 to 2 | 1 | 9.90 |
| 100 | 70.7 | 61.4 | 53.9 | 45.5 | 1 | 99 to 2 | 2 | 22.88 |
| 220 | 69.6 | 59.8 | 52.8 | 46.9 | 1 | 99 to 2 | 3 | 27.39 |
| 310 | 70.3 | 60.6 | 53.4 | 47.5 | 1 | 99 to 2 | 4 | 19.81 |
| 370 | 68.1 | 59.1 | 52.2 | 46.4 | 1 | 99 to 2 | 5 | 14.60 |
| 470 | 71.2 | 59.9 | 52.8 | 46.8 | 1 | 99 to 2 | 6 | 18.48 |
| 570 | 67.7 | 57.2 | 50.6 | 45.4 | 1 | 99 to 2 | 7 | 19.21 |
| 630 | 71.6 | 59.2 | 51.8 | 46.1 | 2 | 99 to 2 | 8 | 9.51 |
| 690 | 69.5 | 56.4 | 50.1 | 44.9 | 0-1 | 99 to 2 | | |
| 720 | 69.9 | 55.8 | 49.9 | 44.7 | 1 | 99 to 2 | 9 | 13.45 |
| 840 | 74.5 | 56.3 | 49.5 | 44.5 | 2 | 99 to 2 | 10 | 16.09 |
| 930 | 78.8 | 54.1 | 48.5 | 44.2 | 2 | 99 to 2 | 11 | 9.31 |
| 1050 | 86.5 | 50.8 | 47.2 | 44.1 | 0-1 | 99 to 2 | 12 | 10.08 |
| 1170 | 95.1 | 62.6 | 47.3 | 44.6 | 2 | 99 to 2 | 13 | 11.35 |
| 1260 | 126.2 | 92.7 | 85.7 | 46.1 | 2 | 10 to 2 | 14 | 9.51 | were assessed (see Example 1.4 below). The corresponding structure was elucidated per NMR.

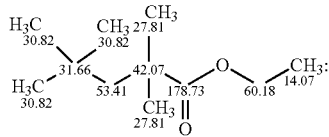

Compound I.1b $^{13}$C NMR (125 MHz, CDCl$_3$): δ = 14.07, 27.81, 30.82, 31.66, 42.07, 53.41, 60.18, 178.73.

Fraction 14 contained 85% of Compound I.5b (RT 30.53 min). The olfactory properties of this mixture (Mixture E) were assessed (see Example 1.5 below). The corresponding structure was elucidated per NMR.

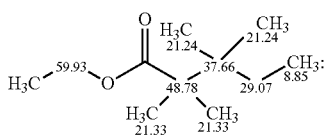

Compound I.5b $^{13}$C NMR (125 MHz, CDCl$_3$): δ = 8.85, 14.27, 21.24, 21.33, 29.07, 37.66, 48.78, 59.96, 177.42.

1 h) Purification of Mixture B:

1.813 kg of the hydrated crude product (Mixture B) obtained in example 1b was subjected to a fine distillation using a column packed with a fabric packing from Montz type A3 (Montz A3 1000 m$^2$/m$^3$). The packing height was 135.5 cm and the column diameter was 43 mm. The distillation was performed in 9 sets over 9 days. The temperature and the pressure at the column head were measured. During start-up of the distillation in each set, the column was operated under total reflux ("total") and then the reflux ratio was adjusted to 15:1. The following fractions were isolated:

| Day | Time | Oil bath Temp. [° C.] | Head Temp. [° C.] | Head Pressure [mbar] | Reflux ratio | Fraction | Collecting time [h] | Amount [g] |
|---|---|---|---|---|---|---|---|---|
| 1 | 07:45 | — | — | 25 | total | 1 | — | |
| 1 | 09:30 | 110 | 78 | | total/15:1 | 1 | — | |
| 1 | 11:40 | 105 | 79 | 25 | 15:1 | ½ | 2.17 | 47 |
| 1 | 15:30 | 108 | 79 | | 15:1 | ⅔ | 3.83 | 79 |
| 2 | 07:45 | — | — | — | | 3 | — | |
| 2 | 08:50 | 108 | 80 | 25 | total/15:1 | 3 | | |
| 2 | 13:00 | 107 | 82 | 25 | 15:1 | ¾ | 4.17 | 106 |
| 2 | 14:45 | 107 | 83 | 25 | 15:1 | 4 | | |
| 3 | 07:40 | — | — | — | — | 4 | — | |
| 3 | 09:00 | 107 | 82 | 25 | total/15:1 | 4 | | |
| 3 | 11:15 | 107 | 84 | 25 | 15:1 | ⅘ | 4.00 | 92 |
| 3 | 14:50 | 107 | 85 | 25 | 15:1 | ⅚ | 3.58 | 93 |
| 3 | 15:45 | 107 | 85 | 25 | 15:1 | 6 | | |
| 4 | 07:40 | — | — | — | — | 6 | — | |
| 4 | 08:35 | 107 | 85 | 25 | total/15:1 | 6 | | |
| 4 | 11:20 | 107 | 85 | 25 | 15:1 | 6/7 | 3.67 | 80 |
| 4 | 15:25 | 107 | 86 | 25 | 15:1 | ⅞ | 4.08 | 97 |
| 5 | 07:20 | — | — | — | — | 8 | — | |
| 5 | 08:35 | 107 | 85 | 25 | total/15:1 | 8 | | |
| 5 | 13:40 | 108 | 86 | 25 | 15:1/10:1 | 8/9 | 5.08 | 127.5 |
| 5 | 15:50 | 108 | 87 | 25 | 10:1 | 9 | | |
| 6 | 07:45 | — | — | — | — | 9 | — | |
| 6 | 08:45 | 108 | 86 | 25 | total/15:1 | 9 | | |
| 6 | 09:30 | 108 | 87 | 25 | 10:1 | 9/10 | 2.92 | 100.5 |
| 6 | 15:15 | 108 | 87 | 25 | 10:1 | 10/11 | 5.75 | 202 |
| 7 | 07:35 | — | — | — | — | 11 | — | |
| 7 | 08:35 | 108 | 88 | 25 | total/15:1 | 11 | | |
| 7 | 13:45 | 108 | 86 | 25 | 10:1 | 11/12 | 5.17 | 192 |
| 8 | 07:35 | — | — | — | — | 12 | — | |
| 8 | 08:45 | 108 | 88 | 25 | total/15:1 | 12 | | |
| 8 | 11:35 | 108 | 87 | 25 | 5:1 | 12/13 | 2.83 | 147 |
| 8 | 15:45 | 112 | 88 | 25 | 5:1 | 13/14 | 4.17 | 206 |
| 9 | 07:20 | — | — | — | — | 14 | — | |
| 9 | 08:30 | 114 | 88 | 25 | total/5:1 | 14 | | |
| 9 | 12:00 | 125 | 88 | 25 | 5:1 | 14 | 3.50 | 91 |

The collected fractions 1 to 14 were analyzed by GC-MS using the following method:

GC System: Agilent 6890N

GC column: ZB-5 (30 m (length), 0.25 mm (ID), 1.0 micrometer (film));

Temperature program: ramp 10° C./min to 150° C., 1° C./min to 200° C., 15° C./min to 300° C.;

Temperature oven: 100° C.;

Temperature of the injector: 250° C.;

Temperature of the detector: 320° C.

The amounts of the individual peaks was determined on the basis of area-%.

Results of the Analysis:

| Fraction | RT 12.6 impurity | RT 12.8 Lower homologue | RT 13.7 I.1b | RT 14.1 | RT 14.7 | RT 15.95 I.3b + I.4b | RT 16.2 I.2b | RT 16.5 | RT 17.2 I.5b | RT 17.4 | RT 18.1 |
|---|---|---|---|---|---|---|---|---|---|---|---|
| input | 0.08 | 0.30 | 16.23 | 0.79 | 1.55 | 39.16 | 27.26 | 0.81 | 13.47 | 0.17 | 0.11 |
| 1 | 1.52 | 4.45 | 89.93 | 0.4 | 0.51 | 1.82 | 0.62 | 0 | 0 | 0 | 0 |
| 2 | 0.83 | 2.63 | 95.79 | 0.45 | 0.08 | 0.10 | 0.07 | 0 | 0 | 0 | 0 |
| 3 | 0.19 | 0.87 | 86.46 | 2.79 | 2.60 | 5.67 | 1.20 | 0 | 0 | 0 | 0 |
| 4 | 0.05 | 0.3 | 51.08 | 4.81 | 6.95 | 29.32 | 7.44 | 0 | 0.08 | 0 | 0 |
| 5 | 0 | 0.04 | 18.14 | 2.89 | 6.34 | 56.86 | 15.61 | 0 | 0.12 | 0 | 0 |
| 6 | 0 | 0 | 8.75 | 1.91 | 4.80 | 63.35 | 20.85 | 0 | 0.33 | 0 | 0 |
| 7 | 0 | 0 | 2.97 | 1.11 | 3.59 | 69.25 | 22.91 | 0 | 0.17 | 0 | 0 |
| 8 | 0 | 0 | 0.89 | 0.55 | 2.19 | 68.13 | 27.54 | 0.02 | 0.49 | 0 | 0 |
| 9 | 0 | 0 | 0.19 | 0.21 | 1.17 | 65.71 | 31.65 | 0.05 | 0.87 | 0 | 0 |
| 10 | 0 | 0 | 0.03 | 0.07 | 0.55 | 60.51 | 37.15 | 0.06 | 0.93 | 0 | 0 |
| 11 | 0 | 0 | 0 | 0 | 0.19 | 53.28 | 44.34 | 0.13 | 2.06 | 0 | 0 |
| 12 | 0 | 0 | 0 | 0 | 0 | 39.83 | 50.47 | 0.46 | 9.24 | 0 | 0 |
| 13 | 0 | 0 | 0 | 0 | 0 | 24.07 | 45.67 | 1.29 | 28.97 | 0 | 0 |
| 14 | 0 | 0 | 0 | 0 | 0 | 6.35 | 21.06 | 2.49 | 70.10 | 0 | 0 |

Fractions 1 and 2 contained a clear note of "old apple" (musty), which is believed to be due to the presence of the impurities at RT 12.6 (lower Mw impurity) and RT 12.8 (a lower homologue, i.e. a compound of formula I.7 where the total number of carbon atoms of $R^1$ and $R^2$ is <6). The fractions following fraction 2 do no longer contain this note of "old apple". By separating fractions 1 and 2, i.e. the impurities which elute at RT 12.6 min. and 12.8 min., from (Mixture B), the organoleptic properties can be further improved. In particular the blueberry note of mixture B can be further elaborated.

A similar separation of 103.8 g of Mixture B was performed using a spinning band column. 9 fractions were collected, which were analyzed by GC-MS using the above method.

Results of the Analysis:

| Fraction | RT 12.6 impurity | RT 12.8 Lower homologue | RT 13.7 I.1b | RT 14.1 | RT 14.7 | RT 15.95 I.3b + I.4b | RT 16.2 I.2b | RT 16.5 | RT 17.2 I.5b | RT 17.4 | RT 18.1 |
|---|---|---|---|---|---|---|---|---|---|---|---|
| input | 0.08 | 0.30 | 16.23 | 0.79 | 1.55 | 39.16 | 27.26 | 0.81 | 13.47 | 0.17 | 0.11 |
| 1 | 0.67 | 2.06 | 73.81 | 2.01 | 2.63 | 14.33 | 3.97 | 0.00 | 0.11 | 0.00 | 0.00 |
| 2 | 0.09 | 0.37 | 28.05 | 1.42 | 2.60 | 43.05 | 22.52 | 0.09 | 1.81 | 0.00 | 0.00 |
| 3 | 0.05 | 0.22 | 20.81 | 1.25 | 2.45 | 47.15 | 25.61 | 0.11 | 2.24 | 0.00 | 0.00 |
| 4 | 0 | 0.06 | 10.61 | 0.92 | 2.06 | 51.88 | 31.44 | 0.18 | 2.85 | 0.00 | 0.00 |
| 5 | 0.02 | 0.10 | 8.63 | 0.76 | 1.85 | 51.97 | 32.18 | 0.22 | 3.98 | 0.00 | 0.00 |
| 6 | 0 | 0.00 | 2.35 | 0.36 | 1.11 | 50.56 | 37.76 | 0.35 | 7.52 | 0.00 | 0.00 |
| 7 | 0 | 0.06 | 3.05 | 0.22 | 0.70 | 43.35 | 37.48 | 0.61 | 14.34 | 0.00 | 0.00 |
| 8 | 0 | 0.00 | 0.27 | 0.04 | 0.19 | 27.41 | 32.06 | 1.36 | 38.68 | 0.00 | 0.00 |
| 9 | 0.02 | 0.10 | 3.91 | 0.14 | 0.28 | 14.33 | 17.05 | 1.69 | 62.06 | 0.00 | 0.00 |

Also here, the fractions 1 and 2 contained a clear note of "old apple" (musty). The fractions following fraction 2 do no longer contain this note.

Odor Properties:

Fraction 1: fruity, blueberry, sweet with a slight but clear note of "old apple" (musty).

Fraction 2: fruity, blueberry, sweet with a slight but clear note of "old apple" (musty).

Fractions 3 to 9: blueberry, fruity, sweet.

1i) Preparation of Mixture G (in the Presence of Methanol and 5% Pd on C with 50% Water Content):

300 g of a mixture of Mixture F were dissolved in 1.5 L of methanol. To this mixture 30 g of Pd/C (5% Pd on C with 50% water content) was added. The reaction vessel was connected to a gasburet filled with water. Then $H_2$ was pressed directly from the gas-bottle into the gasburet in a way that the $H_2$ consumption could be monitored. The reaction proceeded at RT and some exothermy was observed (max. temp 26.7° C.). The experiment was continued for 27 h and a 25.7 L consumption of $H_2$ was observed. The catalyst was filtered off and the solvent was evaporated at reduced pressure. 285.9 g of crude product were obtained. NMR confirmed full conversion, since no traces of the unsaturated product were observed. The olfactory properties of this crude mixture (Mixture G) were assessed (see Example 1.7 below).

A part of this crude reaction mixture (34.4 g) was subjected to distillative separation, only one major fraction was isolated. The olfactory properties of this mixture (Mixture H) were assessed (see Example 1.8 below).

1j) Preparation of Mixture G (in the Presence of 5% Pd/C with 50% Water Content):

50 g of Mixture F are placed in a 270 ml stainless steel autoclave, previously inserted with nitrogen, together with 5 g of catalyst (5% Pd/C with 50% water content, in the form of a pastel. While stirring at 700 rpm at ambient temperature, a hydrogen pressure of 15 bar is first applied. The reaction is then heated to 120° C. and the hydrogen pressure is increased to 30 bar. The reaction is maintained for 24 h at these reaction conditions, during which the hydrogen pressure is kept at 30 bar. The autoclave was then relaxed and cooled. The catalyst was filtered off. The conversion rate to the reaction product (Mixture G) was determined via GC and iodine number. The conversion was >99.8%.

1k) Preparation of Mixture G (in the Presence of Dried 5% Pd/C):

50 g of Mixture F are placed in a 270 ml stainless steel autoclave, previously inserted with nitrogen, together with 5 g of catalyst (5% Pd/C, dry). While stirring at 700 rpm at ambient temperature, a hydrogen pressure of 15 bar is first applied. The reaction is then heated to 120° C. and the hydrogen pressure is increased to 30 bar. The reaction is maintained for 24 h at these reaction conditions, during which the hydrogen pressure is kept at 30 bar. The autoclave was then relaxed and cooled. The catalyst was filtered off. The conversion rate to the reaction product (Mixture G) was determined via GC and iodine number. The conversion was >99.9%.

1l) Preparation of Mixture G (in the Presence of 0.25% Pd on $Al_2O_3$):

50 g of Mixture F are placed in a 270 ml stainless steel autoclave, previously inserted with nitrogen, together with 5 g of catalyst (0.25% Pd on Aluminumoxide). While stirring at 700 rpm at ambient temperature, a hydrogen pressure of 15 bar is first applied. The reaction is then heated to 120° C. and the hydrogen pressure is increased to 30 bar. The reaction is maintained for 24 h at these reaction conditions, during which the hydrogen pressure is kept at 30 bar. The autoclave was then relaxed and cooled. The catalyst was filtered off. The conversion rate to the reaction product (Mixture G) was determined via GC and iodine number. The conversion was >99.9%.

1m) Preparation of Mixture G (in the Presence of Raney-Nickel):

50 g of Mixture F are placed in a 270 ml stainless steel autoclave, previously inserted with nitrogen, together with 2 g of catalyst (Raney-Nickel). While stirring at 700 rpm at ambient temperature, a hydrogen pressure of 15 bar is first applied. The reaction is then heated to 120° C. and the hydrogen pressure is increased to 30 bar. The reaction is maintained for 24 h at these reaction conditions, during which the hydrogen pressure is kept at 30 bar. The autoclave was then relaxed and cooled. The catalyst was filtered off. The conversion rate to the reaction product (Mixture G) was determined via GC. The conversion was >95%.

1n) Preparation of Mixture I and Mixture J:

241.2 g of crude obtained in example 1i were subjected to a fine distillation using a 60 cm column with a 4 cm diameter. 59 cm of the column were filled with column packing (DN30 A3-1000 2.4610 8 27×50 mm). Two temperature measuring points were set at 18 cm and at 48 cm. The following fractions were isolated:

| Time min | Bottom T ° C. | Mes. 1 ° C. | Mes. 2 ° C. | Head T ° C. | Pressure mbar | Reflux ratio sec. | Fraction Nr. | Amount g |
|---|---|---|---|---|---|---|---|---|
| 20 | 45.2 | 46.1 | 44.5 | 23.4 | 0-1 | 99 to 2 | | |
| 60 | 81.6 | 74.7 | 69.8 | 64.7 | 0-1 | 99 to 2 | | |
| 120 | 79.3 | 72.2 | 65.6 | 60.5 | 0-1 | 99 to 2 | | |
| 180 | 78.8 | 71.4 | 64.8 | 59.7 | 1 | 99 to 2 | 1 | 10.39 |
| 240 | 79.1 | 71.5 | 64.9 | 60.1 | 0-1 | 99 to 2 | 2 | 7.71 |
| 300 | 79.4 | 71.6 | 64.9 | 59.8 | 0-1 | 99 to 2 | 3 | 16.96 |
| 360 | 79.5 | 72.5 | 70.6 | 61.5 | 1 | 99 to 2 | 4 | 15.90 |
| 480 | 81.1 | 72.7 | 65.8 | 61.6 | 0-1 | 99 to 2 | | |
| 540 | 81.1 | 72.4 | 65.6 | 60.8 | 1 | 99 to 2 | 5 | 16.94 |
| 600 | 81.1 | 72.1 | 65.4 | 60.7 | 0-1 | 99 to 2 | | |
| 720 | 82.5 | 73.2 | 65.4 | 61.2 | 0-1 | 99 to 2 | 6 | 23.95 |
| 780 | 82.3 | 71.6 | 65.6 | 61.5 | 1 | 99 to 2 | 7 | 12.80 |
| 840 | 82.3 | 71.5 | 64.8 | 60.9 | 0-1 | 99 to 2 | | |
| 900 | 82.5 | 69.1 | 64.5 | 61.2 | 0-1 | 99 to 2 | 8 | 13.49 |
| 960 | 92.5 | 69.1 | 64.6 | 61.5 | 0-1 | 99 to 2 | | |
| 1080 | 94.6 | 76.5 | 64.5 | 61.6 | 1 | 99 to 2 | 9 | 20.94 |
| 1140 | 94.6 | 76.7 | 64.3 | 61.5 | 1 | 99 to 2 | 10 | 20.15 |
| 1200 | 110.2 | 80.5 | 67.5 | 62.9 | 1 | 99 to 2 | 11 | 20.95 |
| 1260 | 130.5 | 106.2 | 103.1 | 67.3 | 1 | 99 to 2 | 12 | 12.28 |

The collected fractions 1 to 14 were analyzed by GC-MS using the following method:

GC column: Rxi1 ms (30 m (length), 0.32 mm (ID), 0.5 micrometer (film));

Temperature program: 50° C. to 100° C. at 1° C./min, 20 min at 200° C.

Temperature of the injector: 250° C.;

Temperature of the detector 280° C.

Flow: 1.5 ml/min.

Results of the Analysis:

| | GC-Area-% of observed peaks at defined retention times (RT) given in [min.] | | | | | | | | | | |
|---|---|---|---|---|---|---|---|---|---|---|---|
| Fraction | RT 27.08 | RT 27.84 | RT 28.44 | RT 28.99 | RT 29.06 | RT 29.48 | RT 29.91 | RT 30.72 | RT 31.56 | RT 32.07 | RT 32.64 |
| input | 6.84 | 4.21 | 19.18 | | 12.84 | 4.98 | 4.87 | 22.53 | 8.36 | 6.02 | 4.92 |
| 1 | 19.28 | 6.21 | 19.74 | 3.69 | 4.43 | 1.73 | 0.72 | 1.86 | 0 | 0 | 0 |

-continued

GC-Area-% of observed peaks at defined retention times (RT) given in [min.]

| Fraction | RT 27.08 | RT 27.84 | RT 28.44 | RT 28.99 | RT 29.06 | RT 29.48 | RT 29.91 | RT 30.72 | RT 31.56 | RT 32.07 | RT 32.64 |
|---|---|---|---|---|---|---|---|---|---|---|---|
| 2 | 24.26 | 8.69 | 29.91 | 5.75 | 6.89 | 2.81 | 1.21 | 3.31 | 0.48 | 0.21 | 0 |
| 3 | 23.02 | 9.72 | 35.43 | 7.11 | 8.89 | 3.68 | 1.66 | 4.51 | 0.66 | 0.26 | 0 |
| 4 | 17.93 | 9.56 | 37.81 | 7.98 | 10.37 | 4.96 | 2.13 | 5.81 | 0.35 | 0 | 0.08 |
| 5 | 12.15 | 8.53 | 37.75 | 8.55 | 12.26 | 6.04 | 2.79 | 8.12 | 1.25 | 0 | 0.52 |
| 6 | 6.01 | 6.35 | 33.73 | 9.09 | 14.31 | 7.91 | 2.73 | 14.69 | 2.11 | 0 | 0.89 |
| 7 | 2.56 | 3.92 | 27.36 | 8.41 | 15.37 | 9.39 | 7.09 | 19.95 | 3.37 | 0 | 1.43 |
| 8 | 0.69 | 1.72 | 13.82 | 5.27 | 12.91 | 9.31 | 9.51 | 34.14 | 6.91 | 0 | 2.88 |
| 9 | 0 | 0.21 | 2.58 | 1.11 | 4.84 | 4.77 | 7.97 | 51.11 | 14.74 | 0 | 7.49 |
| 10 | 0 | 0 | 0.22 | 0.09 | 0.71 | 0.98 | 2.82 | 42.57 | 23.57 | 0 | 16.76 |
| 11 | 0 | 0 | 0.06 | 0 | 0.14 | 0.17 | 0 | 20.57 | 21.31 | 0 | 22.86 |
| 12 | 0 | 0 | 0 | 0 | 0.27 | 0 | 0 | 3.23 | 5.74 | 8.51 | 0.62 |

Fraction 4 contained a mixture of 4 main components/peaks with RT 27.08 min (18% determined per GC), RT 28.44 min (38% determined per GC) and RT 29.06 min (10% determined per GC). The olfactory properties of this mixture (Mixture I) were assessed (see Example 1.9 below).

Some of the compounds in Mixture I could be identified by $^{13}$C NMR (2D $^{13}$C-$^{13}$C INAD-EQUATE):

| Structure | Amount estimated via NMR (+/−10%) |
|---|---|
| 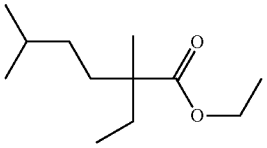 I.8b | 33% |
| 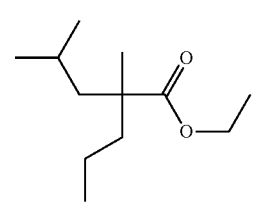 I.9b | 17% |
| 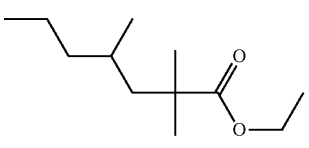 I.10b | 13% |
| 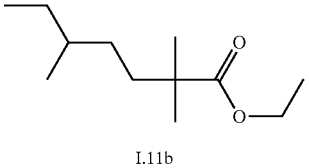 I.11b | 12% |
| 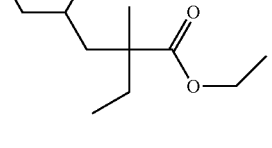 I.12b | 13% |
| 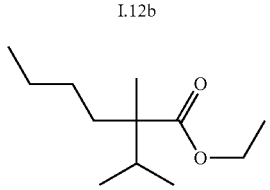 I.13b | 3% |
| 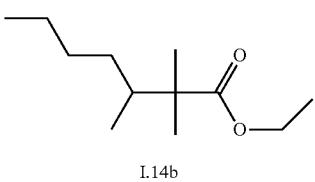 I.14b | 6% |

Fraction 9 contained a mixture of a Compound with RT 29.91 min (8% determined per GC), a Compound with RT 30.72 min (51% determined per GC) and a Compound with RT 31.56 min (15% determined per GC). The olfactory properties of this mixture (Mixture J) were assessed (see Example 1.10 below).

Some of the compounds in Mixture J could be identified by $^{13}$C NMR (2D $^{13}$C-$^{13}$C IN-ADEQUATE):

| Structure | Amount estimated via NMR (+/−10%) |
|---|---|
| 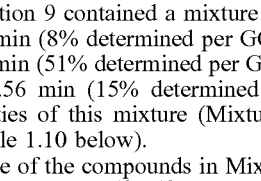 I.13b | 26% |
| 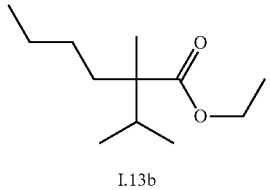 I.14b | 15% |

-continued

| Structure | Amount estimated via NMR (+/−10%) |
|---|---|
| 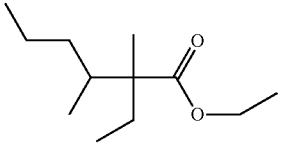 I.15b | 19% |
| 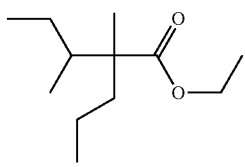 I.16b | 14% |
| 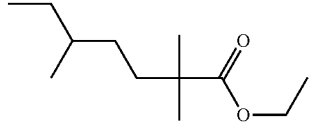 I.11b | 6% |
| 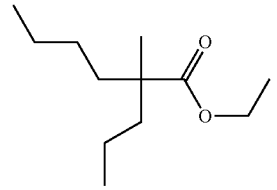 I.17b | 5% |
| 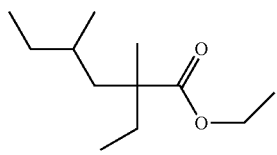 I.12b | 5% |

2. Olfactory Assessment

In order to test the quality and intensity of the odor of the compounds (I) or of the mixture of the compounds (I), scent strip tests were performed.

For this purpose, strips of absorbent paper were dipped into a solution containing 1 to 10% by weight solution of the compound to be tested in ethanol. After evaporation of the solvent (about 30 sec.) the scent impression was olfactively evaluated by a trained perfumer.

Results:

TABLE 1

Results of the scent tests

| Example no. | Compound/Mixture | Identifier | Odor Description |
|---|---|---|---|
| 1.1 | 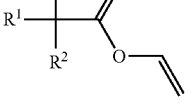 (I.6) Mixtures of isomers of formula (I.6) with $R^1 + R^2 = 6$ carbon atoms, as defined above. | Mixture A | Fresh, fruity, sweet, woody |
| 1.2 | 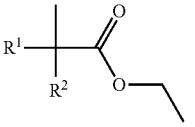 Mixtures of isomers of (I.7) with $R^1 + R^2 = 6$ carbon atoms | Mixture B | Fruity, apple, damascone, blue berry, eucalyptus, camphor, rum |
| 1.3 | (I.1) to (I.3) with $R^3$ = ethyl | Mixture C | Sweet, woody, dried fruit, spicy, ethereal |
| 1.4 | (I.4) with $R^3$ = ethyl | Mixture D | Earthy, yeasty, blue berry, sweet, slightly moldy |
| 1.5 | (I.5) with $R^3$ = ethyl | Mixture E | Woody, sweet, spicy, clove |
| 1.6 | Mixture of isomers; (I.6) with $R^1 + R^2 = 7$ carbon atoms | Mixture F | Dried fruit, fruity, sweet, floral, violet |
| 1.7 | Mixture of isomers; (I.7) with $R^1 + R^2 = 7$ carbon atoms, raw product obtained directly after cat. hydrogenation of Mixture F | Mixture G | Sweet, fruit, red berries, herbal, tea |
| 1.8 | Mixture of isomers; (I.7) with $R^1 + R^2 = 7$ carbon atoms | Mixture H | Red berry, blueberry, cedarwood, dried fruit, sweet, minty |
| 1.9 | Mixture of isomers; (I.7) with $R^1 + R^2 = 7$ carbon atoms, comprising 3 major components: 18%, 38%, 10% | Mixture I | Red berry, minty, dried fruit |
| 1.10 | Mixture of isomers; (I.7) with $R^1 + R^2 = 7$ carbon atoms, comprising 3 major components, different from the major components of ex. 1.8: 8%, 51%, 15% | Mixture J | Blueberry, cedarwood, sweet, ethereal |

The invention claimed is:
1. A method of preparing an aroma chemical composition or for modifying the scent character of an aroma chemical composition, comprising incorporating a compound of the general formula (I)

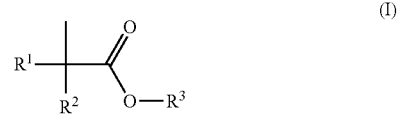

wherein
$R^1$ is $C_1$-$C_4$-alkyl;
$R^2$ is branched $C_3$-$C_8$-alkyl, where the branching is located at least in the α- and/or the β-position to the attachment point of the radical $R^2$ to the rest of the molecule, and $R^3$ is $C_1$-$C_4$-alkyl or $C_2$-$C_4$-alkenyl, where the total number of carbon atoms of the radicals $R^1$ and $R^2$ is in the range of from 6 to 7, or a mixture of two or more compounds of the general formula (I), or a stereoisomer thereof or of a mixture of two or more stereoisomers thereof, into a composition.

2. The method according to claim 1, where a mixture of two or more different compounds of the general formula (I) is used.

3. The method according to claim 1, where a mixture of two or more different compounds of the general formula (I)

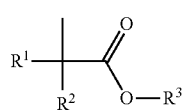
(I)

wherein $R^1$ is selected from $C_1$-$C_3$-alkyl, $R^2$ is selected from branched $C_3$-$C_5$-alkyl, where the branching is located at least in the α- and/or the β-position to the attachment point of the radical $R^2$ to the rest of the molecule, and $R^3$ is $C_1$-$C_4$-alkyl or $C_2$-$C_4$-alkenyl, where the total number of carbon atoms of $R^1$ and $R^2$ is 6, is used.

4. The method according to claim 3, where the mixture comprises the compounds of the general formulae (I.1) to (I.3)

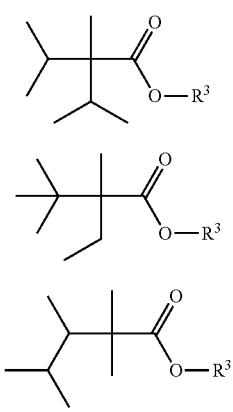

(I.1)

(I.2)

(I.3)

wherein $R^3$ is $C_1$-$C_4$-alkyl.

5. The method according to claim 4, where the mixture additionally comprises the compounds of the general formulae (I.4) to (I.5)

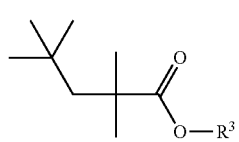
(I.4)

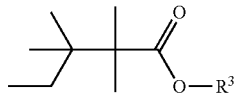
(I.5)

wherein $R^3$ is $C_1$-$C_4$-alkyl.

6. The method according to claim 3, where the mixture comprises the compound of the general formula (I.4)

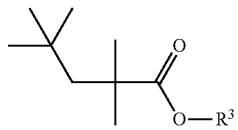
(I.4)

wherein $R^3$ is $C_1$-$C_4$-alkyl, or the compound of the general formula (I.5)

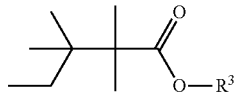
(I.5)

wherein $R^3$ is $C_1$-$C_4$-alkyl.

7. The method according to claim 1, where a mixture of two or more different compounds of the general formula (I)

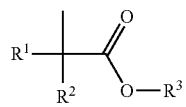
(I)

wherein $R^1$ is selected from $C_1$-$C_4$-alkyl, $R^2$ is selected from branched $C_3$-$C_6$-alkyl, where the branching is located at least in the α- and/or the β-position to the attachment point of the radical $R^2$ to the rest of the molecule, and $R^3$ is $C_1$-$C_4$-alkyl or $C_2$-$C_4$-alkenyl, where the total number of carbon atoms of $R^1$ and $R^2$ is 7, is used.

8. The method according to claim 7, where the mixture comprises the compounds of the general formulae (I.8) to (I.12)

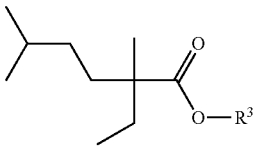
(I.8)

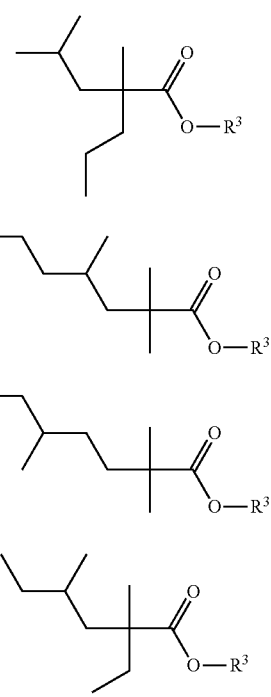

wherein $R^3$ is $C_1$-$C_4$-alkyl, or the compounds of the general formulae (I.13) to (I.16)

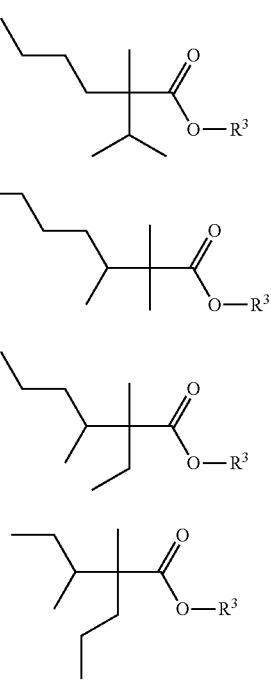

wherein $R^3$ is $C_1$-$C_4$-alkyl.

9. The method according to claim 1, where a compound of the general formula (I)

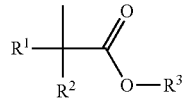

wherein $R^1$ is $C_1$-$C_4$-alkyl, $R^2$ is branched $C_3$-$C_6$-alkyl, where the branching is located at least in the α- and/or the β-position to the attachment point of the radical $R^2$ to the rest of the molecule, and $R^3$ is $C_1$-$C_4$-alkyl or $C_2$-$C_4$-alkenyl, where the total number of carbon atoms of the radicals $R^1$ and $R^2$ is in the range of from 6 to 7, or of a stereoisomer thereof or of a mixture of two or more stereoisomers thereof, is used.

10. The method according to claim 1, wherein the compound of formula (I) or a mixture of two or more compounds of formula (I) or a stereoisomer thereof or a mixture of two or more stereoisomers thereof, are for modifying the scent character of a fragranced composition.

11. The method according to claim 1, in a composition selected from the group consisting of perfume compositions, body care compositions, products for oral and dental hygiene, hygiene articles, cleaning compositions, textile detergent compositions, compositions for scent dispensers, foods, food supplements, pharmaceutical compositions and crop protection compositions.

12. Aroma chemical composition comprising an aroma chemical which is a compound of the general formula (I)

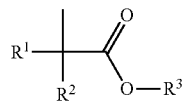

wherein $R^1$ is $C_1$-$C_4$-alkyl;

$R^2$ is branched $C_3$-$C_8$-alkyl, where the branching is located at least in the α- and/or the β-position to the attachment point of the radical $R^2$ to the rest of the molecule; and $R^3$ is $C_1$-$C_4$-alkyl or $C_2$-$C_4$-alkenyl, where the total number of carbon atoms of the radicals $R^1$ and $R^2$ is in the range of from 6 to 7, or a mixture of two or more compounds of the general formula (I), or a stereoisomer thereof or a mixture of two or more stereoisomers thereof, and at least one further aroma chemical and/or a non-aroma chemical carrier.

13. The composition according to claim 12, selected from the group consisting of perfume compositions, body care compositions, products for oral and dental hygiene, hygiene articles, cleaning compositions, textile detergent compositions, compositions for scent dispensers, foods, food supplements, pharmaceutical compositions and crop protection compositions.

14. A mixture of two or more different compounds of the general formula (I)

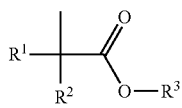
(I)

wherein
$R^1$ is $C_1$-$C_4$-alkyl,
$R^2$ is branched $C_3$-$C_8$-alkyl, where the branching is located at least in the α- and/or the β-position to the attachment point of the radical $R^2$ to the rest of the molecule, and
$R^3$ $C_1$-$C_4$-alkyl,
where the total number of carbon atoms of the radicals $R^1$ and $R^2$ is in the range of from 6 to 7.

15. The mixture according to claim 14, where in the compounds of the general formula (I)
$R^1$ is $C_1$-$C_3$-alkyl,
$R^2$ is branched $C_3$-$C_5$-alkyl, where the branching is located at least in the α- and/or the β-position to the attachment point of the radical $R^2$ to the rest of the molecule, and
$R^3$ is $C_1$-$C_4$-alkyl,
where the total number of carbon atoms of $R^1$ and $R^2$ is 6,
or where in the compounds of the general formula (I)
$R^1$ is selected from $C_1$-$C_4$-alkyl,
$R^2$ is selected from branched $C_3$-$C_6$-alkyl, where the branching is located at least in the α- and/or the β-position to the attachment point of the radical $R^2$ to the rest of the molecule, and
$R^3$ is $C_1$-$C_4$-alkyl,
where the total number of carbon atoms of $R^1$ and $R^2$ is 7.

16. The method according to claim 4, where the overall amount of compounds (I.1), (I.2) and (I.3) in the mixture is at least 50% by weight, based on the total weight of the mixture.

17. The method according to claim 5, where the overall amount of compounds (I.1), (I.2), (I.3), (I.4) and (I.5) in the mixture is at least 80% by weight, based on the total weight of the mixture.

18. The method according to claim 6, where the mixture comprises the compound of the general formula (I.4), where the amount of the compound (I.4) in the mixture is at least 75% by weight, based on the total weight of the mixture, or where the mixture comprises the compound of the general formula (I.5), where the amount of the compound (I.5) in the mixture is at least 75% by weight, based on the total weight of the mixture.

19. The method according to claim 8, where the mixture comprises the compounds of the general formulae (I.8) to (I.12) and where the overall amount of compounds (I.8), (I.9), (I.10), (I.11) and (I.12) in the mixture is at least 70% by weight, based on the total weight of the mixture; or where the mixture comprises the compounds of the general formulae (I.13) to (I.16) and the overall amount of compounds (I.13), (I.14), (I.15) and (I.16) in the mixture is at least 60% by weight, based on the total weight of the mixture.

20. The composition according to claim 12, where the non-aroma chemical carrier is selected from the group consisting of surfactants, oil components and solvents.

21. The composition according to claim 12, comprising a mixture of two or more different compounds of the general formula (I)

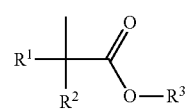
(I)

wherein
$R^1$ is selected from $C_1$-$C_3$-alkyl,
$R^2$ is selected from branched $C_3$-$C_5$-alkyl, where the branching is located at least in the α- and/or the β-position to the attachment point of the radical $R^2$ to the rest of the molecule, and
$R^3$ is $C_1$-$C_4$-alkyl or $C_2$-$C_4$-alkenyl, in particular $C_1$-$C_4$-alkyl,
where the total number of carbon atoms of $R^1$ and $R^2$ is 6.

* * * * *